(12) United States Patent
Smith et al.

(10) Patent No.: US 8,153,121 B2
(45) Date of Patent: Apr. 10, 2012

(54) DIAGNOSIS AND THERAPY OF ANTIBODY-MEDIATED INFLAMMATORY AUTOIMMUNE DISORDERS

(75) Inventors: Terry J. Smith, Manhattan Beach, CA (US); William W. Cruikshank, Westford, MA (US)

(73) Assignee: Los Angeles Biomedical Research Institute at Harbor—UCLA Medical Center, Torrance, CA (US)

( * ) Notice: Subject to any disclaimer, the term of this patent is extended or adjusted under 35 U.S.C. 154(b) by 450 days.

(21) Appl. No.: 10/140,003

(22) Filed: May 6, 2002

(65) Prior Publication Data

US 2003/0021780 A1 Jan. 30, 2003

Related U.S. Application Data

(63) Continuation-in-part of application No. 10/038,509, filed on Jan. 3, 2002, now Pat. No. 7,998,681, which is a continuation-in-part of application No. 10/046,651, filed on Oct. 19, 2001, now Pat. No. 6,936,426, which is a continuation of application No. 09/684,601, filed on Oct. 6, 2000, now abandoned.

(51) Int. Cl.
*A61K 39/35* (2006.01)
*A61K 39/00* (2006.01)
*A61K 39/395* (2006.01)

(52) U.S. Cl. ............... 424/130.1; 424/139.1; 424/141.1; 424/142.1; 424/143.1; 514/2

(58) Field of Classification Search ............... 424/192.1, 424/133.1, 143.1, 145.1; 514/2, 8
See application file for complete search history.

(56) References Cited

U.S. PATENT DOCUMENTS

| | | | |
|---|---|---|---|
| 5,583,018 A * | 12/1996 | Ford | 435/118 |
| 5,643,788 A * | 7/1997 | Baserga et al. | 435/325 |
| 6,159,711 A | 12/2000 | Proudfoot et al. | 435/69.5 |
| 6,699,466 B1 * | 3/2004 | Center et al. | 424/85.2 |

FOREIGN PATENT DOCUMENTS

WO WO 96/17935 6/1996

OTHER PUBLICATIONS

Grubeck-Loebenstein et al., "Retrobulbar T cells from patients with Graves' ophthalmopathy are CD8+ and specifically recognize autologous fibroblasts" J. Clin. Invest. 91994) 93:2738-2743.*
Pritchard et al., "immunoglobulin activation of T cell chemoattractant expression in fibroblasts from pateints with Graves' disease is mediated through the insulin-like growth factor I receptor pathway" J. Immunol. (2003) 170:6348-6354.*
Heufelder et al., "Modulation of Graves' orbital fibroblast proliferation by cytokines and glucocorticoid receptor agonists" investigative ophthalmology and Visual Science (1994) 35:120-127.*
Bahn, R S "Pathophysiology of Graves' ophthalmopathy: the cycle of disease" J Clin Endocrinol Metab (2003) 88:1939-1946.*
Salisbury et al., "Development of molecular agents for IGf receptor targeting" (2003) Horm Metab Res 35:843-849.*
The Merck Manual of Diagnosis and therapy, 17$^{th}$ Edition, (1999) editors Beers and Berkow, Merck Research Laboratories, pp. 1061-1063.*
Stedman's Medical Dictionary, 27$^{th}$ edition, online version, copyright 2000 Lippincott Williams & Wilkins, one page.*
Weightman et al., Exp. Clin. Endocrinol., 1991, 97:197-201.*
Sachdev et al., cancer Research, 203, 63:627-635.*
Liu et al., J. Biol. Chem., 1999, 274:23387-23395.*
Wang et al., Mol. Cancer Ther, 2005, 4:1214-1221.*
Li et al., Biochem Biophys Res Commun, 1993, 196:92-98.*
Alberts et al., Molecular Biology of the Cell, 3$^{rd}$ edition, 1994, pp. 760-761.*
Bell et al., "Functional TSH receptor in human abdominal preadipocytes and orbital fibroblasts," *Am. J. Physiol Cell Physiol.* 279:C335-C340 (2000).
Brennan et al., "p70 (s6k) integrates phosphatidylinositol 3-kinase and rapamycin-regulated signals for E2F regulation in T lymphocytes," *Mol. Cell Biol.*, 19(7):4729-4738 (1999).
Laugwitz et al., "The human thyrotropin receptor: A heptahelical receptor capable of stimulating members of all four G protein families," *Proc. Natl. Acad. Sci. USA*, 93:116.-120 (1996).
Matsumoto et al., "Arthritis provoked by linked T and B cell recognition of a glycolytic enzyme," *Science*, 286:1732-1735 (1999).
Popovich et al., "Concept of autoimmunity following spinal cord injury: possible roles for T lymphocytes in the traumatized central nervous system," *J. Neurosci. Res.*, 45(4):349-363 (1996).
Pritchard et al., "Igs from patients with Graves' disease induce the expression of T cell chemoattractants in their fibroblasts," *J. Immunol.*, 168:942-950 (2002).
Sciaky et al., "Cultured human fibroblasts express constitutive IL-16 mRNA: cyokine induction of active IL-16 protein synthesis through a caspase-3-dependent mechanism," *J. Immunol.*, 164:3806 (2000).
Ullrich et al., "Insulin-like growth factor I receptor primary structure: comparison with insulin receptor suggests structural determinants that define functional specificity," *EMBO J.*, 5(10) :2503-2512 (1986).
Wong et al., "Rantes activates Jak2 and Jak3 to regulate engagement of multiple signaling pathways in T cells," *J. Biol. Chem.*, 276:11427-11431.
Lim et al., "Human Eosinophils Elaborate the Lymphocyte Chemoattractants," *Journal of Immunology* 156:2566-2570 (1996).
Nicoll et al., "Identification of Domains in IL-16 Critical for Biological Activity," *Journal of Immunology* 163:1827-1832 (1999).
Simchen et al., "Expression and Regulation of Regulated on Activation, Normal T Cells Expressed and Secreted in Thyroid Tissue of Patients with Graves' Disease and Thyroid Autonomy and in Thyroid-Derived Cell Population," *Journal of Clinical Endocrinology and Metabolism*, 85:4758-4764 (2000).

(Continued)

*Primary Examiner* — Nora Rooney
(74) *Attorney, Agent, or Firm* — Jones Day

(57) ABSTRACT

The invention provides a method of reducing the severity of an autoimmune condition associated with T-lymphocyte infiltration. The invention also provides a method of diagnosing or predicting the susceptibility to an autoimmune disease associated with fibroblast mediated T-lymphocyte infiltration. Methods of identifying a substance capable of modulating T-lymphocyte recruitment associated with an autoimmune condition also are provided.

6 Claims, 17 Drawing Sheets

OTHER PUBLICATIONS

Weightman et al., "Autoantibodies to IGF-1 Binding Sites in Thyroid Associated Ophthalmopathy," *Autoimmunity* 16:251-257 (1993).

Cai et al., The intracellular signaling pathways involved in MCP-1-stimulated T cell migration across microvascular endothelium, *Cellular Immunology* 167:269-275 (1996).

Franz et al., "Interleukin-16, produced by synovial fibroblasts, mediates chemoattraction for CD4+ T lymphocytes in rheumatoid arthritis," *Eur. J. Immunology*. 28:2661-2671 (1998).

Mira et al., "A role for the chemokine receptor transactivation in growth factor signaling," *EMBO Reports*, 21(21):151-156 (2001).

Perros and Kendall-Taylor, "Thyroid-associated opthalmopathy: pathogenesis and clinical management," *Bailliere's Clinical Endocrinology and Metabolism*, 9:115-135 (1995).

Poggi et al., "Phenotypic and functional analysis of CD4+ NKRP1A+ human T lymphocytes. Direct evicence that the NKRP1A molecule is involved in transendothelial migration," *Eur. J. Immunology* 27:2345-2350 (1997).

Schreiber, "Immunomodulators," *Agents and Actions* (*Suppl.*) 24:254-264 (1988).

* cited by examiner

| Strain | Site | Diagnosis | Treatment | T Cell Migration[a] (% control) | +Anti-IL-16 | +Anti-RANTES | IL-16[b] (pg/ml) | RANTES[c] (pg/ml) |
|---|---|---|---|---|---|---|---|---|
| 1 | Orbit | GD | Control | 108 ± 9 | 102 ± 4 | 110 ± 7 | ND[d] | ND |
|   |   |   | Normal IgG | 110 ± 6 | 104 ± 7 | 103 ± 6 | ND | ND |
|   |   |   | GD-IgG | 179 ± 9 | 142 ± 8 | 158 ± 9 | 58 ± 9 | 83 ± 10 |
|   |   |   | IL-1β | 194 ± 11 | 149 ± 8 | 167 ± 10 | 71 ± 9 | 84 ± 8 |
| 2 | Orbit | GD | Control | 110 ± 7 | 104 ± 8 | 107 ± 9 | ND | ND |
|   |   |   | Normal IgG | 119 ± 10 | 109 ± 10 | 116 ± 11 | ND | ND |
|   |   |   | GD-IgG | 181 ± 11 | 117 ± 12 | 171 ± 9 | 115 ± 15 | ND |
|   |   |   | IL-1β | 195 ± 13 | 171 ± 7 | 170 ± 8 | 82 ± 9 | 116 ± 11 |
| 3 | Abdominal skin | GD | Control | 108 ± 10 | 101 ± 8 | 103 ± 6 | ND | ND |
|   |   |   | Normal IgG | 110 ± 11 | 108 ± 7 | 106 ± 8 | ND | ND |
|   |   |   | GD-IgG | 187 ± 10 | 165 ± 9 | 175 ± 9 | 90 ± 9 | 109 ± 12 |
|   |   |   | IL-1β | 195 ± 13 | 171 ± 7 | 171 ± 8 | 82 ± 9 | 116 ± 11 |
| 4 | Orbit | GD | Control | 111 ± 8 | 105 ± 6 | 103 ± 4 | ND | ND |
|   |   |   | Normal IgG | 109 ± 5 | 122 ± 10 | 113 ± 9 | ND | ND |
|   |   |   | GD-IgG | 280 ± 12 | 130 ± 6 | 197 ± 17 | 213 ± 14 | 98 ± 9 |
|   |   |   | IL-1β | 236 ± 19 | 175 ± 12 | 188 ± 9 | 194 ± 29 | 128 ± 26 |
| 5 | Abdominal skin | GD | Control | 93 ± 6 | 99 ± 7 | 99 ± 6 | ND | ND |
|   |   |   | Normal IgG | 110 ± 9 | 107 ± 8 | 104 ± 8 | ND | ND |
|   |   |   | GD-IgG | 157 ± 6 | 132 ± 8 | 142 ± 9 | ND | ND |
|   |   |   | IL-1β | 144 ± 8 | 128 ± 8 | 131 ± 5 | ND | ND |
| 6 | Neck skin | GD | Control | 103 ± 5 | 100 ± 7 | 104 ± 6 | ND | ND |
|   |   |   | GD-IgG | 195 ± 11 | 153 ± 12 | 168 ± 8 | 97 ± 21 | 198 ± 30 |
|   |   |   | IL-1β | 211 ± 13 | 148 ± 10 | 178 ± 12 | 116 ± 27 | 253 ± 42 |
| 7 | Pretibial skin | GD | Control | 112 ± 9 | 109 ± 7 | 104 ± 8 | ND | ND |
|   |   |   | Normal IgG | 108 ± 7 | 101 ± 6 | 103 ± 9 | ND | ND |
|   |   |   | GD-IgG | 213 ± 11 | 168 ± 9 | 179 ± 10 | 168 ± 23 | 119 ± 17 |
|   |   |   | IL-1β | 236 ± 19 | 175 ± 12 | 188 ± 9 | 194 ± 29 | 128 ± 26 |
| 8 | Pretibial skin | GD | Control | 109 ± 8 | 107 ± 8 | 111 ± 9 | ND | ND |
|   |   |   | Normal IgG | 114 ± 9 | 112 ± 5 | 114 ± 10 | ND | ND |
|   |   |   | GD-IgG | 167 ± 9 | 126 ± 8 | 150 ± 6 | 58 ± 24 | ND |
|   |   |   | IL-1β | 204 ± 14 | 164 ± 10 | 173 ± 8 | 79 ± 11 | ND |
| 9 | Orbit | GD | Control | 109 ± 7 | 104 ± 8 | 104 ± 9 | ND | ND |
|   |   |   | Normal IgG | 106 ± 8 | 101 ± 6 | 109 ± 9 | ND | ND |
|   |   |   | GD-IgG | 111 ± 5 | 106 ± 8 | 104 ± 10 | ND | ND |
|   |   |   | IL-1β | 243 ± 13 | 167 ± 11 | 189 ± 10 | 218 ± 33 | 78 ± 21 |
| 10 | Orbit | GD | Control | 105 ± 8 | 109 ± 10 | 104 ± 5 | ND | ND |
|   |   |   | Normal IgG | 101 ± 9 | 100 ± 7 | 108 ± 9 | ND | ND |
|   |   |   | GD-IgG | 221 ± 13 | 172 ± 8 | 189 ± 11 | 159 ± 28 | 195 ± 35 |
|   |   |   | IL-1β | 248 ± 19 | 189 ± 14 | 206 ± 12 | 246 ± 32 | 214 ± 30 |
| 11 | Orbit | GD | Control | 106 ± 7 | 104 ± 8 | 101 ± 5 | ND | ND |
|   |   |   | Normal IgG | 110 ± 10 | 107 ± 5 | 103 ± 7 | ND | ND |
|   |   |   | GD-IgG | 195 ± 11 | 135 ± 9 | 159 ± 7 | 47 ± 7 | 26 ± 8 |
|   |   |   | IL-1β | 210 ± 13 | 162 ± 11 | 183 ± 6 | 94 ± 12 | 69 ± 6 |
| 12 | Orbit | Normal | Control | 108 ± 9 | 109 ± 4 | 101 ± 7 | ND | ND |
|   |   |   | Normal IgG | 104 ± 6 | 109 ± 5 | 107 ± 6 | ND | ND |
|   |   |   | GD-IgG | 110 ± 9 | 105 ± 8 | 112 ± 8 | ND | ND |
|   |   |   | IL-1β | 168 ± 11 | 143 ± 9 | 156 ± 9 | 56 ± 10 | 42 ± 9 |
| 13 | Orbit | Normal | Control | 92 ± 4 | 90 ± 7 | 94 ± 6 | ND | ND |
|   |   |   | Normal IgG | 106 ± 9 | 95 ± 5 | 99 ± 8 | ND | 10 ± 8 |
|   |   |   | GD-IgG | 92 ± 9 | 97 ± 6 | 101 ± 5 | ND | ND |
| 14 | Orbit | Normal | Control | 102 ± 8 | 104 ± 5 | 105 ± 7 | ND | ND |
|   |   |   | Normal IgG | 108 ± 5 | 108 ± 4 | 103 ± 9 | ND | ND |
|   |   |   | GD-IgG | 109 ± 8 | 104 ± 7 | 106 ± 5 | ND | ND |
|   |   |   | IL-1β | 189 ± 10 | 154 ± 8 | 159 ± 9 | 68 ± 9 | 79 ± 11 |
| 15 | Extremity skin | Normal | Control | 103 ± 4 | 103 ± 8 | 100 ± 6 | ND | ND |
|   |   |   | Normal IgG | 106 ± 9 | 104 ± 7 | 103 ± 8 | ND | ND |
|   |   |   | GD-IgG | 105 ± 7 | 107 ± 7 | 101 ± 5 | ND | ND |
|   |   |   | IL-1β | 197 ± 10 | 153 ± 9 | 172 ± 9 | 138 ± 15 | 173 ± 12 |
| 16 | Extremity skin | Normal | Control | 108 ± 8 | 103 ± 7 | 105 ± 10 | ND | ND |
|   |   |   | Normal IgG | 107 ± 6 | 104 ± 8 | 103 ± 6 | ND | ND |
|   |   |   | GD-IgG | 100 ± 6 | 106 ± 7 | 101 ± 5 | ND | ND |
|   |   |   | IL-1β | 201 ± 7 | 155 ± 8 | 173 ± 7 | 98 ± 19 | 125 ± 9 |

FIGURE 15

| | Lymphocyte Migration[b] (% control) | +Anti-IL-16 | +Anti-RANTES | +Both Abs | IL-16[c] (pg/ml) | RANTES[d] (pg/ml) |
|---|---|---|---|---|---|---|
| Expt. 1 | | | | | | |
| GD-IgG | 274 ± 16 | 186 ± 9 | 217 ± 9 | 162 ± 8 | 538 ± 51 | 462 ± 68 |
| GD-IgG + rapamycin | 190 ± 10 | 184 ± 12 | 157 ± 9 | 155 ± 11 | ND | 449 ± 73 |
| Expt. 2 | | | | | | |
| GD-IgG | 195 ± 11 | 135 ± 9 | 159 ± 7 | | 47 ± 7 | 26 ± 8 |
| GD-IgG + dexamethasone | 121 ± 8 | 117 ± 9 | 118 ± 8 | | ND | ND |

FIGURE 16 though in its entirety.
DIAGNOSIS AND THERAPY OF ANTIBODY-MEDIATED INFLAMMATORY AUTOIMMUNE DISORDERS This application is a continuation-in-part of U.S. application Ser. No. 10/038,509, filed Jan. 2, 2002, which is a continuation-in-part of U.S. application Ser. No. 10/046,651, filed Oct. 19, 2001, which is a continuation of U.S. application Ser. No. 09/684,601, filed Oct. 6, 2000, each of which is incorporated herein by reference in its entirety.

This invention was made with government support under grant numbers EY8976 and EY11708 awarded by the National Institutes of Health. The United States Government has certain rights in this invention.

BACKGROUND OF THE INVENTION

This invention relates generally to molecular medicine and autoimmune disorders and, more specifically, to the identification of an autoantigen receptor that mediates T cell infiltration.

The immune system is a complicated network of cells and molecules that normally work to defend the body and eliminate infections caused by bacteria, viruses, and other invading microbes. If a person has an autoimmune disease, the immune system mistakenly attacks self, targeting the cells, tissues, and organs of a person's own body. A collection of immune system cells and molecules at a target site is broadly referred to as inflammation.

There are many different types of autoimmune diseases that each affect the body in different ways. For example, the autoimmune reaction is directed against the brain in multiple sclerosis and the gut in Crohn's disease. In other autoimmune diseases such as systemic lupus erythematosus, affected tissues and organs may vary among individuals with the same disease. Ultimately, damage to certain tissues by the immune system may be permanent, as with destruction of insulin-producing cells of the pancreas in Type 1 diabetes mellitus.

While the incidence of most individual autoimmune diseases is rare, as a group autoimmune diseases afflict millions of Americans. Most autoimmune diseases strike women more often than men; in particular, they affect women of working age and during their childbearing years.

In a number of autoimmune diseases including, for example, Graves' disease (GD), Rheumatoid Arthritis(RA), myasthenia gravis, insulin-resistant diabetes (Type I), antibodies to cell membrane receptors lead to anti-receptor hypersensitivity reactions that alter cellular function as a result of the binding of antibody to membrane receptors, which can have a stimulatory or a blocking effect. For example, in animal models of myasthenia gravis, the production of antibodies by immunization to the acetylcholine receptor has resulted in the typical muscle fatigue and weakness noted in affected humans, where this antibody has been shown to be present in serum and on muscle membranes and, further, prevents the binding of endogenously produced acetylcholine to its receptor, thereby preventing muscle activation. Similarly, in some diabetic patients with extreme insulin resistance, antibodies to insulin receptors have been shown that prevent the binding of insulin to its receptor.

An important aspect of Graves' disease concerns the presence in most patients of detectable IgGs directed against the thyroid-stimulating hormone receptor (TSHR). These antibodies can possess stimulatory or blocking activities, and depending on which type predominates, result in either thyroid gland over- or under-activity. While the central role for these antibodies in provoking disordered thyroid hormonogenesis and gland enlargement has been established, little direct evidence has been advanced to implicate anti-TSHR Igs in the extra-thyroidal manifestations of Graves' disease. The extra-thyroidal manifestations of Graves' disease involve the infiltration of the connective tissues of the orbit and skin of the lower leg, processes referred to as thyroid-associated ophthalmopathy (TAO) and dermopathy, respectively. These extra-thyroidal processes involve tissue remodeling, including the deposition of hyaluronan, a non-sulfated glycosaminoglycan synthesized by activated fibroblasts. Orbital tissues in TAO are often dramatically inflamed. Immunocompetent cells, including CD4+ and CD8+ T cells, mast cells and B cells, infiltrate the orbital tissue, synthesize and export mediators such as cytokines, which activate fibroblasts. The temporal discordance between the onset of hyperthyroidism and development of TAO also suggests that different causative factors underlie the glandular versus the non-glandular aspects of Graves' disease. Little progress has been made into establishing the basis for TAO and as a result, current therapy is largely nonspecific and inadequate.

The identity the autoantigen that mediates the extra-thyroidal manifestations, in particular, Thyroid-associated Opthalmopathy (TAO) and dermopathy, in which the connective tissue of the orbit and shin, respectively, undergo extensive remodeling driven by recruited T-lymphocytes can provide valuable information for other autoimmune diseases that involve recognition of the same autoantigen. For Graves' disease, the mechanism through which immunocompetent cells are trafficked to affected tissues is critical to understanding and, ultimately, to developing therapies that address both the glandular as well as the non-glandular manifestations of Graves' Disease.

Thus, there exists a need for identification of an autoantigen that is recognized by endogenous immunoglobulins and mediates autoimmune responses. The present invention satisfies this need and provides related advantages as well.

SUMMARY OF THE INVENTION

The invention provides a method of reducing the severity of an autoimmune condition associated with T-lymphocyte infiltration. The invention also provides a method of diagnosing or predicting the susceptibility to an autoimmune disease associated with fibroblast mediated T-lymphocyte infiltration. Methods of identifying a substance capable of modulating T-lymphocyte recruitment associated with an autoimmune condition also are provided.

BRIEF DESCRIPTION OF THE DRAWINGS

FIG. 15 shows a table listing the effects of IgG on IL-16 and RANTES synthesis and T lymphocyte chemotactic production.

Figure 1:
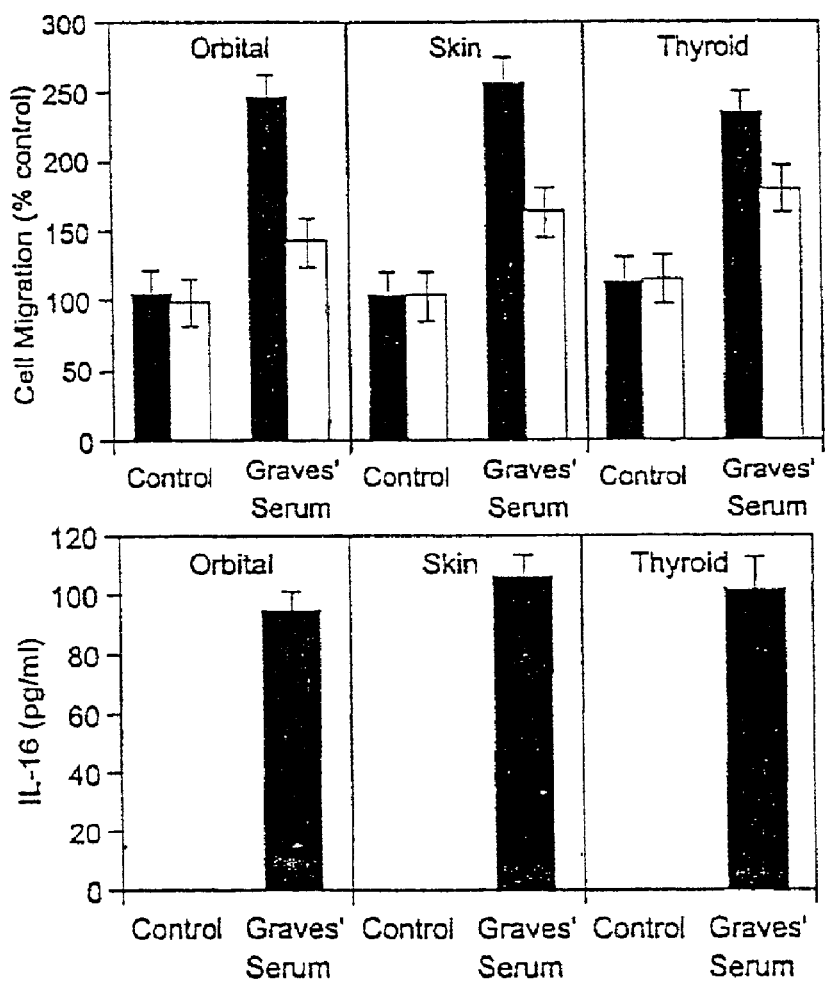
FIG. 1 shows (A) increased T-lymphocyte chemoattractant activity upon addition of unfractionated Graves' disease-serum to fibroblast monolayers obtained from orbit, subcutaneous connective tissue, and thyroid; and (B) elevated levels of the chemoattractant IL-16 in fibroblast medium from Graves' disease serum-treated fibroblasts.

[a] Lymphocyte chemotaxis assay of medium from fibroblasts treated with IL-1⊖ (10 ng/ml), GD-IgG (100 ng/ml), or IgG (100 ng/ml) from donors without known thyroid disease. Chemotactic activity is expressed as a percentage of control, the activity levels of which were found in fibroblast cultures not treated with IL-β or IgG. IL-16 and RATES dependent activities are defined as the differences in chemotaxis observed in samples without and with the respective neutralizing antibodies. Data in FIG. 15 is expressed as means ±SD of three independent determinations. Migration >135% was significant at 5% confidence limit.

[b] Limits of detection, 20 pg/ml.

[c] Limits of detection, 15 pg/ml.

[d] ND, not detected.

FIG. 16 shows a table listing the effects of rapamycin and dexomethasone on IL-16 and RANTES synthesis and T lymphocyte migration activity provoked by IgG in fibroblasts from patients with Graves' disease.

[a] Confluent layers of fibroblasts were treated with nothing, GD-IgG (100 ng/ml) without or with rapamycin (20 nM), or dexamethasone (10 nM) for 24 h. The conditioned medium was then subjected to the T cell migration assay, as described in *Materials and Methods* Without or with anti-IL-16 (10 μg/ml) and/or anti-RANTES-(5 μg/ml) neutralizing Abs. Another aliquot of medium was subjected to the cytokine-specific ELISAs described. Data are expressed as the means ±SD of three independent determinations.

[b] Migration is expressed as a percentage of control, the activity levels of which were found in untreated fibroblast cultures. Migration of >135% was significant at 5% confidence limit.

[c] Limits of detection, 20 pg/ml.

[d] Limits of detection, 15 pg/ml.

DETAILED DESCRIPTION OF THE INVENTION

This invention is directed to a method of reducing the severity of a condition associated with fibroblast mediated T-lymphocyte infiltration by administering to a individual an effective amount of at least one substance that inhibits the interaction between a receptor autoantigen and an endogenous immunoglobulin.

In a related embodiment, the invention provides a method of reducing the severity of a condition associated with fibroblast mediated T-lymphocyte infiltration by administering to a individual an effective amount of at least one substance that prevents the influx of immunocompetent cells to affected tissues by reducing the release by a cell type, for example, fibroblasts of at least one type of chemoattractant molecule that attracts immunocompetent cells.

In a further embodiment, the invention provides a method of reducing the severity of a condition associated with fibroblast mediated T-lymphocyte infiltration by administering to a individual an effective amount of at least one substance that prevents the influx of immunocompetent cells to affected tissues by neutralizing the activity of at least one type of chemoattractant molecule that is normally released by fibroblasts and that attracts immunocompetent cells.

A substance that inhibits the fibroblast-mediated influx of immunocompetent cells to affected tissues can be, for example, a substance that inhibits the interaction between a receptor autoantigen and an endogenous immunoglobulin; a substance that inhibits the interaction between a chemoattractant molecule and its receptor; or a substance that neutralizes at least one type of chemoattractant. Furthermore, a substance that inhibits the influx of T-lymphocytes to affected tissues can be, for example, a substance that inhibits the interaction between the IGF-1R autoantigen, which can be located on a fibroblast or any other cell type, for example, a lymphocyte, and an endogenous disease-specific immunoglobulin G (IgG); a substance that inhibits the interaction between a chemoattractant molecule and its receptor; or a substance that neutralizes at least one type of chemoattractant molecule. A substance that inhibits the influx of T-lymphocytes to affected tissues also can be, for example, any agent that interferes with the signaling cascade that lies downstream of the self-antigen receptor and leads to chemoattractant recruitment or with the activity or expression of any molecule that is activated as a consequence of the interaction between a receptor autoantigen and an endogenous immunoglobulin.

Also provided by the invention disclosed herein are methods of diagnosing or predicting the susceptibility to an autoimmune disease associated with fibroblast mediated T-lymphocyte infiltration in an individual suspected of having a such a disease and methods of identifying a substance that can modulate fibroblast mediated T-lymphocyte infiltration.

The present invention is predicated, in part, on the discovery that the Insulin-Like Growth Factor 1 Receptor (IGF-1R) is an autoantigen recognized by endogenous disease-specific immunoglobulins and, upon activation, can induce the recruitment of T lymphocytes by effecting the release of one or more chemoattractant molecules, for example, RANTES or IL-16. The IGF-1R that serves as the autoantigen can be located, for example, on fibroblasts as described herein, but also can be located on other cell types including on the T lymphocytes themselves.

As used herein, the term "effective amount" is a predetermined amount calculated to achieve the desired therapeutic effect, for example, to alter the interaction between a receptor autoantigen and an endogenous immunoglobulin or other biological activity, resulting in reduction of the severity of a condition associated with fibroblast mediated T-lymphocyte infiltration. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such a substance in depot or long-lasting form as discussed herein. A therapeutically effective amount is typically an amount of a substance that, when administered in a physiologically acceptable composition, is sufficient to achieve a plasma concentration of from about 0.1 µg/ml to about 100 µg/ml, preferably from about 1.0 µg/ml to about 50 µg/ml, more preferably at least about 2 µg/ml and usually 5 to 10 µg/ml. Therapeutic antibodies can be administered in proportionately appropriate amounts in accordance with known practices in this art.

As used herein, "reduction in severity" is intended to refer to an arrest, decrease or reversal in signs and symptoms, physiological indicators, secondary manifestations, biochemical markers or metabolic indicators associated with a particular autoimmune disease. Symptoms of an autoimmune disease depend on the particular organ or tissue attacked by the host's immune system and can include, for example, tissue remodeling, swelling of the joints, neurological impairments, neuroinflammation, gastrointestinal inflammation, skin inflammation, decrease in insulin release in Type 1 diabetes, reduced cortisol and aldosterone in autoimmune adrenal failure. Biochemical markers of an autoimmune disease can include, for example, disease specific immunoglobulins.

The invention method is useful for the treatment of a variety of autoimmune conditions that involve the activation of one or more cell types that express an autoantigen receptor, for example, fibroblasts, resulting in the recruitment of immunocompetent cells. Immunocompetent cells are recruited to sites of inflammation through a mechanism that is initiated by activation of one or more cell types as a result of binding of endogenous antibodies to receptor autoantigens on cell surface of that cell type, for example, fibroblasts. As described herein, Insulin-Like Growth Factor 1 Receptor (IGF-1R), a tyrosine kinase, represents an autoantigen that is expressed on fibroblast cells and initiates the fibroblast activation and subsequent cascade of events resulting in recruitment of immunocompetent cells. The IGF-1R nucleic acid and amino acid sequences are described, for example, by Ullrich et al., *EMBO J* 5(10):2503-2512(1986), which is incorporated by reference. IGF-1R also is expressed on cell types other than fibroblasts, such as for example, on lymphocytes themselves, where it can similarly serve as a mediator of T lymphocyte recruitment and infiltration.

Insulin-like growth factors (IGF)-1 and IGF-2 possess structural similarities with pro-insulin. IGFs are synthesized largely by the liver in response to growth hormone and play important paracrine roles in a variety of tissues. IGF-1 exists largely bound to binding proteins and exerts its biological actions through an association with IGF-1 receptor (IGF-1R), a surface tyrosine kinase receptor (Adams et al., *Cell Mol Life Sci.* 57:1050-1093 (2000)). IGF-1R resembles the insulin receptor and mediates the growth-promoting activities of both IGF-1 and IGF-2.

The human IGF-1R surface tyrosine receptor amino acid and corresponding nucleic acid sequence are publicly available, for example, in the NCBI Genbank database under Accession Nos. CAA28030 and X04434, respectively. The mature IGF-1R has a sequence of 1367 amino acids as described by Ullrich et al., *EMBO J.* 5(10): 2503-2512 (1986), which is incorporated herein by reference. This receptor involves a family of insulin receptor substrate proteins which in turn interact with the mitogen activated protein kinases. IGF-1R has been implicated in the pathogenesis of growth and neoplastic disorders.

This invention is based, in part, on the surprising discovery that IGF-1R plays a direct role in the pathogenesis of human autoimmunity. Many different cell types are known to express IGF-1R, including those of the fibroblast lineage. Therefore, the methods of the invention can be practiced with IGF-1R-mediated orchestration of an autoimmune response regardless of whether the IGF-1R is present on fibroblasts or on another cell type, for example, monocytes or macrophages.

In one embodiment, the invention method is useful for the treatment of an autoimmune disease in which activated cells, for example, fibroblasts, that express the autoantigen recognized by the disease-specific antibodies, for example, drive the recruitment of immunocompetent cells, for example, in Graves' disease (GD), Rheumatoid Arthritis (RA), autoimmune thyroiditis, Diabetis Mellitus Type 1, autoimmune adrenal failure, pemphigus, Lupus, autoimmune nephritis, autoimmune carditis, pseudotumor of the orbit, neuritis, autoimmune pneumonitis.

As used herein, the term "autoimmune disease" refers to a disorder that occurs because of autoimmunity—a disease that is caused by an immune response to the body of the patient himself or herself. Autoimmunity is an etiology, which means that it is a cause of disease and autoimmune diseases are classified based on their common etiology. The results of an autoimmune reaction vary and range from fever to destruction of diverse types tissues, such as blood vessels, cartilage, myelin and skin. Autoimmunity can affect any organ in the body including, for example, the brain, skin, kidney, lungs, liver, heart, intestine and thyroid. Therefore, autoimmune disease is anatomically diverse and the clinical expression of the disease depends upon the site affected. The resulting inflammation and tissue damage can cause kidney failure, breathing problems, abnormal heart function, pain, deformity, delirium, and death. Autoimmune diseases can affect connective tissues, which are those tissues that bind together various tissues and organs.

A large number of conditions almost certainly have an autoimmune cause or component, including, for example, Graves' disease, rheumatoid arthritis (RA), Insulin dependent Diabetes (Type I), Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg- Strauss Syndrome Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Guillain-Barré, Hashimoto's Thyroiditis, Idiopathic Pulmonary Fibrosis, Idiopathic Thrombocytopenia Purpura (ITP), IgA Nephropathy, Juvenile Arthritis, Lichen Planus, Lupus, Méniére's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis Vitiligo, Wegener's Granulomatosis.

Various autoimmune diseases are characterized by the presence of specific pathogenic antibodies that interact with fibroblast to mediate one or more manifestations of the particular disease as described, for example, for RA by Matsumoto et al., *Science* 286: 1732 (1999); and for Graves, disease by Pritchard et al., *J. Immunol.* 168:942-950 (2002), both of which are incorporated herein by reference. For example, in Graves' disease disease-specific endogenous immunoglobulins (GD-IgGs) recognize and bind to the IGF-1R in order to activate fibroblasts that, as a result, express and release the T-lymphocyte chemoattractant molecules RANTES and IL-16. Thus, the invention provides a method of reducing the severity of an autoimmune condition associated with fibroblast mediated T-lymphocyte infiltration by administering to a individual an effective amount of at least one substance that inhibits the interaction between IGF-1R and an endogenous immunoglobulin, for example, IgG.

As described herein, IGF-1R represents an autoantigen that is associated with the tissue manifestations of Graves' disease at the sites of the orbit, pre-tibial skin and thyroid. In particular, IGF-1R mediates both the glandular and extrathyroidal, components of Graves' disease by driving the infiltration of T-lymphocytes to connective tissue. The thyroid-stimulating hormone receptor (TSHR), which is involved in the thyroidal component of Graves' disease provides a further example of an autoantigen involved in mediation of the manifestations of an autoimmune disease, as described by Laugwitz et al., *Proc. Natl. Acad. Sci. USA* 93:116 (1996), which is incorporated herein by reference.

The mediation of a condition associated with recruitment of T lymphocytes resulting from the binding and activation of an endogenous immunoglobulin to the autoantigen receptor IGF-1R can involve IGF-1R located on fibroblasts as well as on other cell types, for example, monocytes and macrophages. Therefore, the invention also provides a method of reducing the severity of a condition associated with T-lymphocyte infiltration by administering an effective amount of a substance that inhibits the interaction between IGF-1R and an endogenous disease specific immunoglobulin.

A substance that is useful in the invention methods for reducing the severity of a condition associated with fibroblast-mediated T lymphocyte recruitment and infiltration or with IGF-1R-mediated T-lymphocyte recruitment where the IGF-1R autoantigen can be located on a non-fibroblast cell can be, for example, a substance that inhibits the interaction between the IGF-1R autoantigen, which can be located on a fibroblast or other cell type, for example, monocytes or macrophages, and an endogenous disease-specific immunoglobulin G (IgG); a substance that inhibits the interaction between a chemoattractant molecule and its receptor; or a substance that neutralizes at least one type of chemoattractant molecule. A substance useful in the invention methods for reducing the severity of a condition associated with fibroblast-mediated T lymphocyte recruitment and infiltration or with IGF-1R-mediated T-lymphocyte recruitment where the IGF-1R autoantigen can be located on a non-fibroblast cell can be, for example, an anti-idiotype antibody directed against the antigen-specific part of the sequence of a disease specific antibody, for example, an GD-IgG or an RA-IgG. Antigenic specificities are defined by the unique sequences (idiotopes) of the antigen combining site and anti-idiotype antibodies recognize these specific sequences (idiotopes) of the disease-specific antigen binding site and can, for example, resemble the epitope to which the disease-specific IgG reacts. The substances described herein, which modulate the influx of immunocompetent cells, are collectively referred to herein as modulatory substances.

Graves' Disease is characterized by hyperthyroidism caused by a generalized overactivity of the entire thyroid gland. The leading cause of hyperthyroidism, Graves' disease represents a basic defect in the immune system, causing production of immunoglobulins which stimulate and attack the thyroid gland, thereby leading to the growth of the gland and the overproduction of thyroid hormone. In addition to the glandular manifestations, Graves' disease also is associated with extrathyroidal manifestations, Thyroid-associated opthalmopathy (TAO) and dermopathy, in which the autoantibodies attack the tissues in the eye muscles and in the pretibial skin, respectively, and cause extensive remodeling of the connective tissue. Connective tissue remodeling associated with TAO and dermopathy represents a secondary manifestation of a fibroblast-mediated condition associated with T-lymphocyte infiltration, such as Graves' disease, that can be partly or wholly alleviated by administering an effective amount of at least one substance that inhibits the interaction between IGF-1R and an endogenous immunoglobulin.

As exemplified herein, Rheumatoid Arthritis is a further autoimmune disease that can be reduced in severity by administering to a individual an effective amount of at least one substance that inhibits the interaction between IGF-1R and an endogenous immunoglobulin, for example, immunoglobulin G. Rheumatoid arthritis (RA) involves inflammation of the lining of body joints, most commonly the small joints of the hands. Inflammation and thickening of the joint lining, called the synovium, can cause pain, stiffness, swelling, warmth, and redness. The affected joint may also lose its shape, resulting in loss of normal movement and, if uncontrolled, may cause destruction of the bones, deformity and, eventually, disability. In some individuals, RA can also affect other parts of the body, including the blood, lungs, skin and heart. As described herein, RA-specific antibodies (RA-IgGs) activate RA fibroblasts by recognition of and binding to the IGF-1R, which serves as an autoantigen expressed on the surface of the RA fibroblasts.

The methods of the invention also are useful for reducing the severity of a neuroinflammatory disorder, for example, an demyelinating disease. A central mechanism in the pathology of neuroinflammatory demyelinating diseases is the organ-specific migration of activated T lymphocytes into the brain. Similar to models of neuroinflammatory disease such as experimental autoimmune encephalomyelitis (EAE), injury to the spinal cord precipitates the activation of resident microglia and the recruitment of circulating inflammatory cells, including macrophages and lymphocytes. In the EAE rat model, these cells can cause tissue damage and loss of neurological function via autoimmune reactions to myelin proteins. Consistent with the concept of trauma-induced autoimmune reactions, T lymphocytes isolated from Adspinal-injured rats can cause neurologic deficits and histopathologic changes similar to EAE when injected intravenously into naive animals as described by Popovich et al., *J. Neurosci. Res.* 45(4):349-363 (1996), which is incorporated herein by reference. Based on the existence of trauma-induced autoimmunity by which the autoreactive repertoire regulates ongoing central nervous system (CNS) immunologic responses, the methods of the invention are applicable in the context of CNS trauma and neurodegenerative diseases such as for example, Multiple Sclerosis (MS), Chronic Inflammatory Demyelinating Polyneuropathy, Amyotrophic Laterial Sclerosis (ALS) and Alzheimer's Disease.

Demyelinating diseases are an important group of neurological disorders because of the frequency with which they occur and the disability that they cause. Demyelinating diseases have in common a focal or patchy destruction of myelin sheaths that is accompanied by a neuroinflammatory response. Neuroinflammatory demyelinating diseases can be divided into processes affecting myelin of the central nervous system and those affecting myelin of the peripheral nervous system. Multiple Sclerosis (MS) is a central nervous system demyelinating disease with an autoimmune etiology as reviewed in Martin et al., *Annu. Rev. Immunol.* 10:153-187 (1992), which is incorporated herein by reference. Other demyelinating diseases of the central nervous system include, for example, acute disseminated encephalomyelitis (ADE) including postinfectious and postvaccinal encephalomyelitis, acute necrotizing hemorrhagic encephalomyelitis and progressive (necrotizing) myelopathy. Demyelinating diseases of the peripheral nervous system include, for example, acute inflammatory demyelinating polyradiculoneuropathy (Guillain-Barré syndrome), chronic inflammatory demyelinating polyradiculoneuropathy (CIDP), demyelinating neuropathy associated with IgM monoclonal gammopathy and neuropathy associated with sclerosing myeloma.

A modulating substance can inhibit, for example, the interaction between a receptor autoantigen and an endogenous immunoglobulin or the interaction between a chemoattractant molecule and its receptor. A modulating substance that inhibits, for example, the interaction between a receptor autoantigen and an endogenous immunoglobulin can act either directly to disrupt or prevent the interaction or can act indirectly as, for example, a blocking agent that renders functionally inactive either the receptor autoantigen or the immunoglobulin. Such an inhibitory modulating substance, which is useful for practicing the invention, can effect a decrease in the extent, amount or rate of autoantigen receptor or immunoglobulin expression or activity; a decrease in the extent, amount or rate of expression or activity of a chemoattractant molecule or its receptor; or a decrease in the extent, amount or rate of release of a chemoattractant molecule. An effective amount is the amount of a modulating substance necessary to effect a reduction in the extent, amount or rate of fibroblast activation. For example, an effective amount of a substance that inhibits the interaction between a receptor autoantigen and an endogenous immunoglobulin or the interaction between a chemoattractant molecule and its receptor; or the release of a chemoattractant molecule can cause a two-fold, five-fold, ten-fold, 20-fold, 100-fold or more reduction in the amount or rate of fibroblast activation. A modulating substance that inhibits the interaction between, for example, a receptor autoantigen and an endogenous immunoglobulin can be an agent that effects a decrease in the extent, amount or rate of the receptor autoantigen expression or effecting a decrease in the activity of receptor autoantigen, for example, IGF-1R. Inhibitory modulating substances useful for practicing the claimed invention include, for example, binding molecules such as antibodies, fragments of antibodies or antibody-like molecules that bind the autoantigen receptor, for example, IGF-1R, but do not lead to activation of the fibroblast.

An example of a modulating substance that inhibits the interaction between a receptor autoantigen and an endogenous immunoglobulin is any molecule that binds either the receptor autoantigen or the endogenous immunoglobulin with sufficient affinity to decrease fibroblast activation. Additionally, an inhibitory modulating substance can be any molecule binds to a regulatory molecule or gene region so as to inhibit or promote the function of the regulatory protein or gene region and effect a decrease in the extent or amount or rate of receptor expression or activity. An example of a substance that inhibits the interaction between the IGF-1R autoantigen and an endogenous immunoglobulin can include an antisense nucleic acid molecule, a dominantnegative IGF-1R mutant or a transcriptional inhibitor that binds to an IGF-1R 5' promoter/regulatory region.

Such a modulating substance can be produced using methods which are generally known in the art, and include the use of a purified autoantigen receptor polypeptide, for example, IGF-1R, to produce antibodies or to screen libraries of compounds, as described previously, for those which specifically bind a corresponding autoantigen polypeptide but do not trigger T lymphocyte recruitment and infiltration. For example, in one aspect, an antibody that is selective for an autoantigen receptor polypeptide of the invention can be used directly as an antagonist, or indirectly as a targeting or delivery mechanism for bringing a cytotoxic or cytostatic agent to disease-specific fibroblast cells that express the corresponding autoantigen receptor. Such agents can be, for example, radioisotopes. The antibodies can be generated using methods that are well known in the art and include, for example, polyclonal, monoclonal, chimeric, humanized single chain, Fab fragments, and fragments produced by a Fab expression library.

Biologically-effective antisense molecules, as well as dominant negative mutant versions of a receptor autoantigen, for example, the IFG-1R are suitable substances for practicing the invention methods. Antisense nucleotide sequences as well as sequences encoding for a dominant negative IGF1-R can be placed in an appropriate plasmid vector and employed to inhibit the interaction between a,receptor autoantigen and an endogenous immunoglobulin; or as a substance that prevents the influx of immunocompetent cells-to affected tissues.

In one aspect, an antisense molecule to a nucleic acid molecule that encodes, for example, a receptor autoantigen, a chemottractant molecule, a chemoattractant molecule receptor, can be used to block the transcription or translation of the corresponding mRNA. Specifically, cells can be transformed with sequences complementary to a nucleic acid molecule encoding, for example, IGF-1R. Such methods are well known in the art, and sense or antisense oligonucleotides or larger fragments, can be designed from various locations along the coding or control regions of sequences encoding autoantigen receptor polypeptides or nucleic acids. These antisense molecules may be DNA, stable derivatives of DNA such as derivatives of RNA such as 2'-O-alkyl RNA, or other oligonucleotide mimetics. U.S. Pat. Nos. 5,652,355 and 5,652,356, which describe the synthesis and effect of physiologically-stable antisense molecules, are incorporated herein by reference. Thus, antisense molecules may be used to indirectly inhibit the interaction between, for example, a receptor autoantigen and an endogenous immunoglobulin or a chemoattractant molecule and its corresponding receptor; or to prevent the influx of immunocompetent cells to affected tissues by reducing the release by fibroblasts of at least one type of chemoattractant molecule that attracts immunocompetent cells.

A dominant negative mutant of the IGF-1R, for example, the dominant negative mutant of IGF-1R designated IGF-1R, 486/STOP described herein, also can serve as a substance that can inhibit the interaction between a receptor autoantigen and an endogenous immunoglobulin; or as a substance that prevents the influx of immunocompetent cells to affected tissues by reducing the release by fibroblasts of at least one type of chemoattractant molecule that attracts immunocompetent cells.

Host cells transformed with a nucleotide sequence that encodes a dominant negative mutant of the present invention may be cultured under conditions suitable for the expression and recovery of the encoded protein from cell culture. Embodiments of the present invention are host cells transformed with a purified polynucleotide comprising a nucleic acid sequence that corresponds to a dominant negative IGF-1R polypeptide. Those skilled in the art will appreciate that cells of this type or preparations made from these cells also can be used in the methods of the invention for identifying a modulating substance described herein.

Expression vectors derived from retroviruses, adenovirus, adeno-associated virus (AAV), herpes or vaccinia viruses, or from various bacterial plasmids can be used for delivery of antisense nucleotide sequences to the fibroblast or other cell population. The viral vector selected should be able to infect the targeted cells, for example, fibroblast cells and be safe to the host and cause minimal cell transformation. Retroviral vectors and adenoviruses provide an efficient, useful, and well-characterized means of introducing and expressing foreign genes into mammalian cells. These vectors are well known in the art and have very broad host and cell type ranges, express genes stably and efficiently. Methods which are well known to those skilled in the art can be used to construct such recombinant vectors and are described in Sambrook et al., Sambrook et al., *Molecular Cloning: A Laboratory Manual,* 2nd ed., Cold Spring Harbor Press, Plainview, N.Y. (1989), which is incorporated herein by reference. Even in the absence of integration into the DNA, such vectors can continue to transcribe RNA molecules until they are disabled by endogenous nucleases. Transient expression can last for a month or more with a non-replicating vector and even longer if appropriate replication elements are part of the vector system.

Eukaryotic recombinant host cells are especially preferred. Examples include, but are not limited to yeast, mammalian cells including but not limited to cell lines of human, bovine, porcine, monkey and rodent origin, and insect cells including but not limited to Drosophila and silkworm derived cell lines. Cell lines derived from mammalian species are particularly suitable and can be obtained from a variety of commercial sources known in the art.

The expression vector may be introduced into host cells via any one of a number of techniques including, for example, transformation, transfection, lipofection, protoplast fusion, and electroporation. Commercially available kits, including well-characterized vectors, transfection reagents and conditions, and cell culture materials are well-established and readily available, for example, from Clonetech (Palo Alto, Calif.); Invitrogen (Carlsbad, Calif.); Pharmingen (San Diego, Calif.) and Stratagene (La Jolla, Calif.). The expression vector-containing cells are clonally propagated and individually analyzed to determine the level of polypeptide production. Identification of host cell clones which express, for example, a dominant negative mutant can be performed by several means, including but not limited to immunological reactivity with antibodies, and/or the presence of host cell-associated specific biological activity. A variety of protocols for detecting and measuring the expression of the dominant negative mutant, using either polyclonal or monoclonal antibodies specific for the protein are known in the art. Examples include, for example, enzyme-linked immunosorbent assay (ELISA), radioimmunoassay (RIA) and fluorescent activated cell sorting (FACS).

Ribozymes, which are enzymatic RNA molecules, can be used to catalyze the specific cleavage of an autoantigen receptor mRNA, for example, IGF-1R mRNA. The mechanism of ribozyme action involves sequence-specific hybridization of the ribozyme molecule to complementary target autoantigen receptor RNA, followed by endonucleolytic cleavage. Specific ribozyme cleavage sites within any potential RNA target are identified by scanning an autoantigen receptor RNA for ribozyme cleavage sites which include the following sequences: GUA, GUU, and GUC. Once identified, short RNA sequences of between 15 and 20 ribonucleotides corresponding to the region of the target gene containing the cleavage site can be evaluated for secondary structural features which can render the oligonucleotide inoperable. The suitability of candidate targets can also be evaluated by testing accessibility to hybridization with complementary oligonucleotides using ribonuclease protection assays. Antisense molecules and ribozymes of the invention can be prepared by any method known in the art for the synthesis of nucleic acid molecules.

As described herein, a modulating substance that inhibits the interaction between, for example, a receptor autoantigen and an endogenous immunoglobulin or between a chemoattractant molecule and its receptor, can be a compound or molecule that binds either the receptor or its ligand, for example, IGF-1R, with sufficient affinity to reduce or inhibit the specific interaction that leads to receptor activation and subsequent T lymphocyte recruitment and infiltration. The autoantigen can be located on a fibroblast or any other cell type. A modulating substance that inhibits the interaction between, for example, a receptor autoantigen and an endogenous immunoglobulin or between a chemoattractant molecule and its receptor can be a macromolecule, such as polypeptide, nucleic acid, carbohydrate or lipid. Thus, a substance that inhibits the interaction between a receptor autoantigen and an endogenous immunoglobulin can be an antibody, antisense nucleic acid, a dominant negative mutant of a receptor autoantigen, or any compound identified by the methods described below. A modulating substance that inhibits, for example, the interaction between a receptor autoantigen and an endogenous immunoglobulin or between a chemoattractant molecule and its receptor, can also be a derivative, analogue or mimetic compound as well as a small organic compound as long as the interaction between the receptor and ligand that leads to T lymphocyte recruitment and infiltration is reduced or inhibited in the presence of the substance. The size of a modulating substance such as one that inhibits the interaction between a receptor autoantigen and an endogenous immunoglobulin is not important so long as the molecule exhibits or can be made to exhibit inhibitory activity with regard to the interaction that leads to fibroblast activation. For example, a substance that inhibits the interaction between a receptor autoantigen and an endogenous immunoglobulin can be as little as between about one and six, and as large as tens or hundreds of monomer building blocks which constitute a macromolecule or chemical binding molecule.

Similarly, an organic compound can be a simple or complex structure so long as it has sufficient activity with regard to inhibiting the interaction, for example, between a receptor autoantigen and an endogenous immunoglobulin or between a chemoattractant molecule and its receptor, that leads to T lymphocyte recruitment and infiltration.

Examples of a modulating substance that inhibits the interaction between a receptor autoantigen and an endogenous immunoglobulin include, for example, IGF-1R antisense nucleic acid and transcriptional inhibitors that bind to the IGFIR promoter/regulatory region. Additionally, receptors, ligands, growth factors, cytokines or chemokines, for example, which inhibit fibroblast mediated T-lymphocyte recruitment and infiltration are useful for practicing the methods of the invention. Furthermore, as described above, DNA binding polypeptides such as transcription factors and DNA replication factors are also modulatory substances useful for practicing the invention methods so long as they have selective activity with regard to inhibiting the interaction between a receptor autoantigen and an endogenous immunoglobulin that leads to fibroblast activation; inhibiting the interaction between a chemoattractant molecule and its receptor; neutralizing a chemottractant molecule; inhibiting the release by a fibroblast of a chemotattractant molecule; or any of the mechanisms described herein or known to those of skill in the art for inhibiting T-lymphocyte recruitment and infiltration. Finally, polypeptides, nucleic acids and chemical compounds such as those selected from random and combinational libraries can also be modulating substances that inhibit the interaction between a receptor autoantigen and an endogenous immunoglobulin that leads to receptor activation resulting in T-lymphocyte recruitment and infiltration.

As described herein, a modulating substance useful for practicing the invention methods can have selective activity with regard to directly or indirectly inhibiting the interaction between a receptor autoantigen and an endogenous immunoglobulin that leads to fibroblast activation; inhibiting the interaction between a chemoattractant molecule and its receptor; neutralizing a chemottractant molecule; inhibiting the release by a fibroblast of a chemotattractant molecule; or any of the mechanisms described herein or known to those of skill in the art for inhibiting T-lymphocyte recruitment and infiltration.

Various approaches can be used for identifying a modulating substance that reduces the severity of a condition associated with fibroblast mediated T-lymphocyte infiltration upon being administered in an effective amount. For example, one approach is to use the information available regarding the structure and function of IGF-1R to generate binding molecule populations from molecules known to function as protease binding molecules or known to exhibit or be capable of exhibiting binding affinity specific for a particular autoantigen receptor polypeptide. As set forth herein, a modulating substance that, upon being administered in an effective amount, reduces the severity of a condition associated with fibroblast mediated T-lymphocyte infiltration can be an antibody and other receptor of the immune repertoire that prevents fibroblast activation resulting in T-lymphocyte infiltration compound. An antibody that recognizes a catalytic site of a molecule associated with mediation of fibroblast activation is especially useful for practicing the invention method of reducing the severity of a condition associated with fibroblast mediated T-lymphocyte infiltration by administering to a individual an effective amount of at least one substance that inhibits the interaction between a receptor autoantigen and an endogenous immunoglobulin. The normal function of such immune receptors is to bind essentially an infinite number of different antigens and ligands. Therefore, generating a diverse population of binding molecules from an immune repertoire, for example, can be useful for identifying a modulating substance that, if administered in an effective amount, reduces the severity of a condition associated with fibroblast mediated T-lymphocyte infiltration.

A modulating substance that inhibits, for example, the interaction between a receptor autoantigen and an endogenous immunoglobulin and prevents fibroblast activation, can further be identified from a large population of unknown molecules by methods well known in the art. Such a population can be a random library of peptides or small molecule compounds. The population can be generated to contain a sufficient diversity of sequence or structure so as to contain a molecule that will bind to an endogenous autoantigen receptor molecule such as, for example, IGF-1R, or its corresponding nucleic acid. Those skilled in the art will know what size and diversity is necessary or sufficient for the intended purpose. A population of sufficient size and complexity can be generated so as to have a high probability of containing a modulating substance that binds, for example, an endogenous autoantigen receptor molecule such as IGF-1R, with sufficient affinity to modulate activity. Numerous other types of library molecule populations exist and are described further below.

While the descriptions set forth herein mostly utilize as an example a receptor autoantigen and corresponding immunoglobulin, it is understood that the types of modulatory substances and identification methods described herein are applicable to any modulating substance described herein for practicing the invention methods, including a modulatory substance that has selective activity with regard to inhibiting the interaction between a receptor autoantigen and an endogenous immunoglobulin; inhibiting the interaction between a chemoattractant molecule and its receptor; neutralizing a chemottractant molecule; inhibiting the release by a fibroblast of a chemotattractant molecule; or any additional mechanism described herein or known to those of skill in the art for directly or indirectly inhibiting T-lymphocyte recruitment and infiltration.

Any molecule that binds to an endogenous autoantigen receptor, to a gene region that controls expression of such an autoantigen, or to a regulatory molecule that modulates activity or expression of an endogenous autoantigen receptor, as well as to any regulatory molecule that modulates expression an endogenous autoantigen receptor, for example, IGF-1R, and reduces or inhibits fibroblast activation is a modulating substance useful for practicing the invention. For example, a substance that inhibits the interaction between a receptor autoantigen and an endogenous immunoglobulin can be a regulatory molecule that affects the expression of an autoantigen such as IGFIR by modulating the action of a transcription factor that controls or upregulates transcription of the autoantigen receptor nucleic acid.

An example of a modulating substance that inhibits the interaction between a receptor autoantigen and an endogenous immunoglobulin useful for practicing the claimed invention can be an antibody against a regulator molecule that modulates expression or activity of a receptor autoantigen or an endogenous disease-specific immunoglobulin. Alternatively, it may be desired to use populations of random peptide populations to identify a modulating substance that inhibits the interaction between a receptor autoantigen and an endogenous immunoglobulin. Given the guidance provided herein, those skilled in the art will know or can determine what type of approach and what type of modulating substance is appropriate for practicing the methods of the invention.

A moderate sized population for identification of a modulating substance that inhibits the interaction between a receptor autoantigen and an endogenous immunoglobulin can consist of hundreds and thousands of different binding molecules within the population, whereas a large sized binding molecule population will consist of tens of thousands and millions of different binding molecule species. More specifically, large and diverse populations of binding molecules for the identification of a modulating substance that inhibits the interaction between a receptor autoantigen and an endogenous immunoglobulin will contain any of about $10^4$, $10^5$, $10^6$, $10^7$, $10^8$, $10^9$, $10^{10}$, or more, different molecule species. One skilled in the art will know the approximate diversity of the population of test-substances sufficient to identify a modulating substance of the invention, a term collectively referred to herein to describe a substance that inhibits the interaction between a receptor autoantigen and an endogenous immunoglobulin; a substance that inhibits the interaction between a receptor autoantigen and an endogenous immunoglobulin; a substance that inhibits the interaction between a chemoattractant molecule and its receptor; or a substance that neutralizes at least one type of chemoattractant.

Recombinant libraries of test substances can be used to identify a modulating substance of the invention, since large and diverse populations can be rapidly generated and screened. Recombinant libraries of expressed polypeptides useful for identifying a modulating substance that inhibits the interaction between a receptor autoantigen and an endogenous immunoglobulin can be engineered in a large number of different ways known in the art. Recombinant library methods similarly allow for the production of a large number of test substance populations from naturally occurring repertoires. Whether recombinant or otherwise, essentially any source of test substance population can be used so long as the source provides a sufficient size and diversity of different compounds to identify a modulating substance that inhibits the interaction between a receptor autoantigen and an endogenous immunoglobulin.

A phage expression library in which lysogenic phage cause the release of bacterially expressed binding molecule polypeptides is a specific example of a recombinant library that can be used to identify a modulating substance that inhibits the interaction between a receptor autoantigen and an endogenous immunoglobulin. In another type of phage expression library, large numbers of potential modulating substances that inhibit the interaction between a receptor autoantigen and an endogenous immunoglobulin can be expressed as fusion polypeptides on the periplasmic surface of bacterial cells. Libraries in yeast and higher eukaryotic cells exist as well and are similarly applicable in the methods of the invention. Those skilled in the art will know or can determine what type of library is useful for identifying a modulating substance that inhibits the interaction between a receptor autoantigen and an endogenous immunoglobulin.

In addition to the methods described above, which utilize purified polypeptide to screen libraries of compounds for those that inhibit the interaction between a receptor autoantigen and an endogenous immunoglobulin, an inhibitory modulating substance can be identified by using purified polypeptide to produce antibodies. For example, antibodies which are specific for IGF-1R or another endogenous autoantigen receptor can be used as a modulating substance that inhibits the interaction between a receptor autoantigen and an endogenous immunoglobulin and can be generated using methods that are well known in the art. Such a modulating substance that inhibits the interaction between a receptor autoantigen and an endogenous immunoglobulin can be both a polyclonal or monoclonal antibody against IGF-1R, for example, the IGF-1R blocking antibody #36491 (Pharmingen, San Diego, Calif.), or any other endogenous autoantigen receptor, as well as antigen binding fragments of such antibodies including Fab, F(ab')2, Fd and Fv fragments and the like, as long as the antibody or fragment, by virtue of the inhibiting the interaction between a receptor autoantigen and an endogenous immunoglobulin, reduces or inhibits fibroblast activation is a modulating substance useful for practicing the invention methods. In addition, a modulating substances useful for practicing the methods of the invention can be a non-naturally occurring antibody, including, for example, a single chain antibody, chimeric antibody, bifunctional antibody, complementarity determining region-grafted (CDR-grafted) antibody or humanized antibody, as well as an antigen-binding fragment thereof. Such an antibody, antibody-like molecule or fragment thereof is useful as a modulating substance as long as it inhibits the recruitment and infiltration of T lymphocytes.

Methods of preparing and isolating antibodies, including polyclonal and monoclonal antibodies, using peptide immunogens, are well known to those skilled in the art and are described, for example, in Harlow and Lane, *Antibodies: A Laboratory Manual*, (Cold Spring Harbor Laboratory Press, 1988), which is incorporated herein by reference. Non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275-1281 (1989), which is incorporated herein by reference. These and other methods of making, for example, chimeric, humanized, CDR-grafted, single chain, and bifunctional antibodies are well known to those skilled in the art (Hoogenboom et al., U.S. Pat. No. 5,564,332, issued Oct. 15, 1996; Winter and Harris, *Immunol. Today* 14:243-246 (1993); Ward et al., *Nature* 341:544-546 (1989); Hilyard et al., *Protein Engineering: A practical approach* (IRL Press 1992); Borrabeck, *Antibody Engineering,* 2d ed. (Oxford University Press 1995); each of which is incorporated herein by reference).

A substance that inhibits the interaction between a receptor autoantigen and an endogenous immunoglobulin so as to inhibit or reduce T lymphocyte recruitment or infiltration can be labeled so as to be detectable using methods well known in the art (Hermanson, *Bioconlugate Techniques*, Academic Press, San Diego (1996); Harlow and Lane, supra,1988; chap. 9). For example, a modulating substance that inhibits the interaction between a receptor autoantigen and an endogenous immunoglobulin can be linked to a radioisotope or therapeutic agent by methods well known in the art. A modulating substance that inhibits the interaction between a receptor autoantigen and an endogenous immunoglobulin by directly binding to an endogenous autoantigen or to a disease specific immunoglobulin, when linked to a radioisotope or other moiety capable of visualization, can be useful to diagnose or stage the progression of a clinical stage of a condition associated with fibroblast mediated T-lymphocyte infiltration.

Methods for raising polyclonal antibodies, for example, in a rabbit, goat, mouse or other mammal, are well known in the art (Harlow and Lane, supra, 1988). The production of anti-peptide antibodies commonly involves the use of host animals such as rabbits, mice, guinea pigs, or rats. If a large amount of serum is needed, larger animals such as sheep, goats, horses, pigs, or donkeys can be used. Animals are usually chosen based on the amount of antiserum required and suitable animals include rabbits, mice, rats, guinea pigs, and hamsters. These animals yield a maximum of 10-50 μL, 100-200 μL and 1-2 mL of serum per single bleed, respectively (Harlow and Lane, supra, 1988). Rabbits are very useful for the production of polyclonal antisera, since they can be safely and repeatedly bled and produce high volumes of antiserum. Two injections two to four weeks apart with 15-50 μg of antigen in a suitable adjuvant such as, for example, Freund's Complete Adjuvant can be followed by blood collection and analysis of the antiserum.

In addition, monoclonal antibodies can be obtained using methods that are well known and routine in the art (Harlow and Lane, supra, 1988). A peptide portion of a protein such as IGF-1R or, as described further below, of a chemoattractant molecule, for example, RANTES, IL-16, or their respective recptors, for use as an immunogen can be determined by methods well known in the art. Spleen cells from an immunized mouse can be fused to an appropriate myeloma cell line to produce hybridoma cells. Cloned hybridoma cell lines can be screened using a labeled protein to identify clones that secrete the corresponding antibodies, respectively. Hybridomas expressing the monoclonal antibodies having a desirable specificity and affinity can be isolated and utilized as a continuous source of the antibody.

Humanized antibodies can be constructed by conferring essentially any antigen binding specificity onto a human antibody framework. Methods of constructing humanized antibodies are useful to prepare an antibody appropriate for practicing the methods of the invention and avoiding host immune responses against the antibody neutralizing agent when used therapeutically. The antibodies described herein can be used to generate therapeutic modulating substances for reducing the severity of a condition associated with fibroblast mediated T-lymphocyte infiltration by methods well known in the art such as complementary determining region (CDR)-grafting and optimization of framework and CDR residues. For example, humanization of an antibody neutralizing agent can be accomplished by CDR-grafting as described in Fiorentini et al., *Immunotechnology* 3 (1): 45-59 (1997), which is incorporated herein be reference. Briefly, CDR-grafting involves recombinantly splicing CDRs from a nonhuman antibody neutralizing agent into a human framework region to confer binding activity onto the resultant grafted antibody, or variable region binding fragment thereof. Once the CDR-grafted antibody, or variable region binding fragment is made, binding affinity comparable to the nonhuman antibody neutralizing agent can be reacquired by subsequent rounds of affinity maturation strategies known in the art. Humanization of a rabbit polyclonal antibody can be accomplished by similar methods as described in Rader et al., *J. Biol. Chem.* 275(18): 13668-13676 (2000), which is incorporated herein be reference.

Humanization of a nonhuman antibody useful as a modulating substance for practicing a method of the invention can also be achieved by simultaneous optimization of framework and CDR residues, which permits the rapid identification of co-operatively interacting framework and CDR residues, as described in Wu et al., *J. Mol. Biol.* 294(1): 151-162 (1999), which is incorporated herein by reference. Briefly, a combinatorial library that examines a number of potentially important framework positions is expressed concomitantly with focused CDR libraries consisting of variants containing random single amino acid mutations in the third CDR of the heavy and light chains. By this method, multiple Fab variants containing as few as one nonhuman framework residue and displaying up to approximately 500-fold higher affinity than the initial chimeric Fab can be identified. Screening of combinatorial framework-CDR libraries permits identification of monoclonal antibodies with structures optimized for function, including instances in which the antigen induces conformational changes in the monoclonal antibody. The enhanced humanized variants contain fewer nonhuman framework residues than antibodies humanized by sequential in vitro humanization and affinity maturation strategies known in the art.

It is further contemplated that a modulating substance useful for practicing a method of the invention can be a human antibody. Human antibodies can be produced by methods known in the art that involve immunizing a transgenic nonhuman animal with the desired antigen. The transgenic nonhuman animal can be modified such that it fails to produce endogenous antibodies, but instead produces B-cells which secrete fully human immunoglobulins. The antibodies produced can be obtained from the animal directly or from immortalized B-cells derived from the transgenic nonhuman animal. Alternatively, the genes encoding the immunoglobulins with human variable regions can be recovered and expressed to obtain the antibodies directly or modified to obtain analogs of antibodies such as, for example, single chain $F_v$ molecules. Thus, it is contemplated to produce a modulating substance useful for practicing a method of the invention that is a fully human immunoglobulin to a specific antigen or to produce an analog of the immunoglobulin by a process that includes immunizing a nonhuman animal with antigen under conditions that stimulate an immune response.

The nonhuman animal that produces a human antibody can be modified to be substantially incapable of producing endogenous heavy or light immunoglobulin chain, but capable of producing immunoglobulins with both human variable and constant regions. In the resulting immune response, the animal produces B cells which secrete immunoglobulins that are fully human and specific for the antigen, for example, IGF-1R, RANTES or IL-16. The human immunoglobulin of desired specificity can be directly recovered from the animal, for example, from the serum, or primary B cells can be obtained from the animal and immortalized. The immortalized B cells can be used directly as the source of human antibodies or, alternatively, the genes encoding the antibodies can be prepared from the immortalized B cells or from primary B cells of the blood or lymphoid tissue, for example, spleen, tonsils, lymph nodes, bone marrow, of the immunized animal and expressed in recombinant hosts, with or without modifications, to produce the immunoglobulin or its analogs. In addition, the genes encoding the repertoire of immunoglobulins produced by the immunized animal can be used to generate a library of immunoglobulins to permit screening for those variable regions which provide the desired affinity. Clones from the library which have the desired characteristics can then be used as a source of nucleotide sequences encoding the desired variable regions for further manipulation to generate human antibodies or analogs with these characteristics using standard recombinant techniques. Various techniques for preparing human antibodies using transgenic nonhuman animals, for example, transgenic mice, are well known in the art and described, for example, in Fishwild et al., *Nature Biotechnology* 14: 845-851 (1996); Heijnen et al., *Journal of Clinical Investigation* 97: 331-338 (1996); Lonberg et al. *Nature* 368:856-859 (1994); Morrison, *Nature* 368:812-813 (1994); Neuberger, *Nature Biotechnology* 14: 826 (1996); Chadd and Chamow, *Curr. Opin. Biotechnol.* 12(2):188-94 (2001); Russel et al., *Infection and Immunity* 1820-1826 (2000); Gallo et al., *European Journal of Immunoloqy* 30:534-540 (2000); Davis et al., *Cancer Metastasis Rev.* 18(4):421-5 (1999); Green, *Journal of Immunological Methods* 231:11-23 (1999) Yang et al., *Journal of Leukocyte Biol-* ogy 66:401-410 (1999); Jakobovits, *Advanced Drug Delivery Reviews* 31:33-42 (1998); Green and Jakobovits, *J. Exp. Med.* 188(3):483-495 (1998); Jakobovits, *Exp. Opin. Invest. Drugs* 7(4):607-614 (1998); Mendez et al., *Nature Genetics* 15:146-156 (1997); Jakobovits, *Weir's Handbook of Experimental Immunology, The Integrated Immune System, Vol. IV:* 194.1-194.7 (1996), each of which is incorporated herein by reference. Furthermore, various techniques known in the art for preparation of a human antibody are described in U.S. Pat. Nos. 6,162,963; 6,150,584; 6,114,598; 6,111,166; 6,096,311 and 6,075,181, each of which is incorporated herein by reference.

As described herein, an antibody can be modulating substance useful for practicing a method of the invention and can include, for example, a polyclonal antibody, monoclonal antibody as well as recombinant versions and functional fragments thereof. Recombinant versions of antibodies include a wide variety of constructions ranging from simple expression and co-assembly of encoding heavy and light chain cDNAs to speciality constructs termed designer antibodies. Recombinant methodologies, combined with the extensive characterization of polypeptides within the immunoglobulin superfamily, and particularly antibodies, provides the ability to design and construct a vast number of different types, styles and specificities of binding molecules derived from immunoglobulin variable and constant region binding domains. Specific examples include chimeric antibodies, where the constant region of one antibody is substituted with that of another antibody, and humanized antibodies, described above, where the complementarity determining regions (CDR) from one antibody are substituted with those from another antibody.

Other recombinant versions of antibodies include, for example, functional antibody variants where the variable region binding domain or functional fragments responsible for maintaining antigen binding is fused to an $F_c$ receptor binding domain from the antibody constant region. Such variants are essentially truncated forms of antibodies that remove regions non-essential for antigen and $F_c$ receptor binding. Truncated variants can be have single valency, for example, or alternatively be constructed with multiple valencies depending on the application and need of the user. Additionally, linkers or spacers can be inserted between the antigen and $F_c$ receptor binding domains to optimize binding activity as well as contain additional functional domains fused or attached to effect biological functions other than, for example, binding to a receptor autoantigen so as to inhibit its interaction with an endogenous immunoglobulin; binding to a chemoattractant molcecule or its receptor to neutralize the cell recruitment activity of the chemoattractant molecule; or binding to a chemoattractant molcecule receptor to prevent the release of the chemottractant molecule from a fibroblast cell. Those skilled in the art will know how to construct recombinant antibodies in light of the art knowledge regarding antibody engineering and given the guidance and teachings herein. A description of recombinant antibodies, functional fragments and variants and antibody-like molecules can be found, for example, in "Antibody Engineering," 2nd Edition, (Carl A. K. Borrebaeck, Ed.) Oxford University Press, New York,(1995).

Additional functional variants of antibodies that can be used as modulating substances useful for practicing a method of the invention include antibody-like molecules other than antigen binding-$F_c$ receptor binding domain fusions. For example, antibodies, functional fragments and fusions thereof containing a $F_c$ receptor binding domain can be produced to be bispecific in that one variable region binding domain exhibits binding activity for one antigen and the other variable region binding domain exhibits binding activity for a second antigen. Such bispecific antibody neutralizing agents can be advantageous in the methods of the invention because a single bispecific antibody will contain two different target antigen binding species. Therefore, a single molecular entity can be administered to achieve neutralization of, for example, both RANTES and IL-16.

An antibody useful as a modulating substance for practicing the method of the invention can also be an immunoadhesion or bispecific immunoadhesion. Immunoadhesions are antibody-like molecules that combine the binding domain of a non-antibody polypeptide with the effector functions of an antibody of an antibody constant domain. The binding domain of the non-antibody polypeptide can be, for example, a ligand or a cell surface receptor having ligand binding activity. Immunoadhesions can contain at least the $F_c$ receptor binding effector functions of the antibody constant domain. Specific examples of ligands and cell surface receptors that can be used for the antigen binding domain of an immunoadhesion include, for example, a T cell receptor such as the CCR5 receptor that recognizes RANTES. It is understood that other ligands and ligand receptors known in the art can similarly be used for the antigen binding domain of an immunoadhesion. In addition, multivalent and multispecific immunoadhesions can be constructed for use as a modulating substance for reducing the severity of a condition associated with fibroblast mediated T-lymphocyte infiltration. The construction of bispecific antibodies, immunoadhesions, bispecific immunoadhesions and other heteromultimeric polypeptides which can be used in the invention methods is the individual matter of, for example, U.S. Pat. Nos. 5,807,706 and 5,428,130, which are incorporated herein by reference.

The invention also provides a method of reducing the severity of a condition associated with fibroblast mediated T-lymphocyte infiltration by administering to a individual an effective amount of at least one modulating substance that modulating substance prevents the influx of immunocompetent cells to affected tissues by neutralizing the activity of at least one type of chemoattractant molecule that is normally released by fibroblasts and that attracts immunocompetent cells.

As further described below, the chemoattractant molecule can be cytokine, including a chemotactic cytokine, more commonly referred to as a chemokine. In one embodiment of the invention method, the chemoattractant molecule is a C-C chemokine, for example, the chemoattractant molecule RANTES. In a further embodiment of the invention methods, the chemoattractant molecule is a cytokine that serves as a specific CD4+ ligand, for example, the chemoattractant molecule IL-16.

A successful host response to inflammation generally requires the accumulation of specialized host cells at the site of tissue damage. This cellular accumulation is a critical step in the normal inflammatory process and is mediated by a family of over forty structurally and functionally related proteins known as cytokines. Cytokines are soluble glycoproteins in the range of 5-20 kDa that are released by cells of the immune system and that act nonenzymatically through specific receptors to regulate immune responses. Cytokines resemble hormones in that they act at low concentrations bound with high affinity to a specific receptor.

Interleukin 16 (IL-16), formerly known as lymphocyte chemoattractant factor or LCF, is a CD4+ cell-specific cytokine detected in asthma, RA, Crohn's Disease and systemic lupus erythematosus. IL-16 is synthesized as a precursour molecule of 69 kDa and subsequently undergoes cleavage by caspase-3, which results in release of 17 kDa to 20 kDa polypepeptides form the cell. Activity is subsequently conferred by the multimerization of four identical subuntis to a 56 kDa mlecule. IL-16 is a CD4+ specific ligand that activates T lymphocytes, monocytes and eosinophils displaying CD4+. CD4+ and CD8+ lymphocytes, airway epithelium, B lymphocytes and mast cells can express IL-16. In addition, IL-16 expression has been demonstrated in cytokine activated fibroblasts as described by Sciaky et al., *J. Immunol.* 164: 3806 (2000), which is incorporated herein by reference.

Chemokines represent a subset of cytokines. Chemokines are homologous 8 to 10 kDa heparin binding proteins that possess a conserved structural motif containing two cysteine pairs and are divided into subfamilies based on the relative position of the cysteine residues in the mature protein. There are at least four subfamilies of chemokines, but only two, α-chemokines and β-chemokines, have been well characterized. In the α-chemokines, the first two cysteine residues are separated by a single amino acid (CXC), whereas in the β-chemokines the first two cysteine residues are adjacent to each other (CC). The C-X-C chemokines include, for example, interleukin-8 (IL-8), human platelet derived factors, IP-10 and Mig. Members of the C-C chemokine subfamily include, for example, regulated on activation, normal T-cell expressed and secreted (RANTES), macrophage chemoattractant and activating factor (MCAF), macrophage inflammatory protein-1α (MIP-1α) and macrophage inflammatory protein-1β (MIP-1β).

Chemokines induce cell migration and activation in at least two ways: first, through direct chemoattraction, and, second, by binding to specific G-protein coupled cell-surface receptors on target cells. Chemokines selectively attract leukocyte subsets; some chemokines act specifically toward eosinophils, others toward monocytes, dendritic cells, or T cells as reviewed by Luster, *New Enql. J. Med.* 338: 436-445 (1998), which is incorporated herein by reference. In general, CC chemokines chemoattract monocytes, eosinophils, basophils, and T cells; and signal through specific chemokine receptors. More than 10 distinct chemokine receptors, each expressed on different subsets of leukocytes, have been identified. Chemokine receptors are constitutively expressed on some cells, whereas they are inducible on others.

RANTES utilizes at least four GTP-protein coupled receptors, including CCR5, and activates basophils, eosinophils, monocytes as well as resting and activated naive and memory T lymphocytes. In T lymphocytes, RANTES engagement of CCR5 activates Janus kinase kinases and p38 mitogen-activated protein kinase and multiple downstream signaling pathways as described by Wong et al., *J. Biol. Chem.* 276: 11427 (2001), which is incorporated herein by reference.

As described herein, release of the chemoattractant molecules IL-16 and RANTES by activated immunocompetetent cells leads to the recruitment and infiltration of T-lymphocytes. Once a tissue has been infiltrated with immunocompetent cells including T cells and monocytes, these cells secrete high levels of pro-inflammatory cytokines such as TNF-α and IL-1. CD40, a member of the tumor necrosis factor-alpha (TNF-alpha) receptor family of surface molecules, is expressed by a variety of cell types, including nonlymphoid cells such as fibroblasts, endothelia, and epithelial cells in culture. Recent evidence suggests participation of the CD40/CD40 ligand bridge in the cross-talk between resident thyroid cells and bone marrow-derived cells recruited to the thyroid. Therefore, once a tissue has been infiltrated with immunocompetent cells that secrete high levels of pro-inflammatory cytokines such as TNF-α and IL-1, a feedback loop can be initiated as fibroblasts respond by further propagating the inflammatory cascade.

As described herein, the release by fibroblasts of a chemoattractant molecule that attracts immunocompetent cells, for example, T lymphocytes, can be inhibited by reducing or preventing the interaction between a receptor autoantigen and an endogenous immunoglobulin. In a further embodiment, the invention also can be practiced by administering to a individual an effective amount of at least one modulating substance that prevents the influx of immunocompetent cells to affected tissues by reducing the release by fibroblasts of at least one type of chemoattractant molecule that attracts immunocompetent cells. In a related embodiment, the invention is practiced by administering to a individual an effective amount of at least one modulating substance that prevents the influx of immunocompetent cells to affected tissues by neutralizing the activity of at least one type of chemoattractant molecule that is normally released by fibroblasts and that attracts immunocompetent cells.

A modulating substance that neutralizes the activity of at least one type of chemoattractant molecule, for example, RANTES or IL-16, modulates the chemoattractant molecule sufficiently to reduce its activity related to cell recruitment. Such a neutralizing substance can be a macromolecule, such as polypeptide, nucleic acid, carbohydrate or lipid. A modulating substance that neutralizes the activity of at least one type of chemoattractant molecule can also be a derivative, analogue or mimetic compound as well as a small organic compound as long as cell-recruitment activity is reduced in the presence of the neutralizing agent. The types of molecules that can be neutralizing substances useful for practicing the methods of the invention as well as the methods of administration described herein with reference to chemoattractant molecules are equally applicable to both cytokines and chemokines. A neutralizing substance can be as little as between about one and six, and as large as tens or hundreds of monomer building blocks which constitute a macromolecule or chemical binding molecule. Similarly, an organic compound can be a simple or complex structure so long as it binds the targeted chemoattractant molecule with sufficient affinity to reduce activity. A substance that neutralizes a chemottractant molecule can be a polypeptide, nucleic acid or chemical compound as described herein and, further, can be identified via any of the methods described herein for identifying a modulating substance of the invention. In particular, a substance that neutralizes a chemottractant molecule can be an antisense polynucleotide directed to a polynucleotide encoding said chemokine, a nucleotide aptamer that affects the binding of said chemokine to at least one chemokine receptor, a peptide aptamer that affects the binding of said chemokine to at least one chemokine receptor, and a small molecule that affects the binding of said chemokine to at least one chemokine receptor Therefore, the library and screening methods described herein for identification of a substance that inhibits the interaction between a receptor autoantigen and an endogenous immunoglobulin, are equally applicable to identification of a substance that prevents the influx of immunocompetent cells to affected tissues by neutralizing the activity of at least one type of chemoattractant molecule, for example, RANTES or IL-16.

Neutralizing substances specific for a chemoattractant molecule, for example, RANTES or IL-16, can include antibodies and other receptor or ligand binding polypeptides of the immune system. Such other molecules of the immune system include for example, T cell receptors (TCR) including CD4 cell receptors. Additionally, cell surface receptors such as integrins, growth factor receptors and chemokine receptors, as well as any other receptors or fragments thereof that bind the chemoattractant molecule, or can be made to bind the chemoattractant molecule, with sufficient affinity to reduce activity are also neutralizing substances useful for practicing the methods of the invention. Additionally, receptors, growth factors, cytokines or chemokines, for example, which inhibit the expression of the chemoattractant molecule or its receptor, for example, RANTES or IL-16, are also neutralizing substances useful for practicing the methods of the invention. Furthermore, DNA binding polypeptides such as transcription factors and DNA replication factors are likewise included within the definition of the term binding molecule so long as they have selective binding activity for the targeted chemoattractant molecule, for example, RANTES or IL-16, or regulatory molecules that control the expression or activity of the targeted chemoattractant molecule or gene regions that control the expression of the targeted chemoattractant molecule. Finally, polypeptides, nucleic acids and chemical compounds such as those selected from random and combinational libraries, as described above, are also included within the definition of the term so long as such a molecule binds the targeted chemoattractant molecule with sufficient affinity to decrease cell recruitment activity.

Various approaches can be used for identifying a modulating substance that prevents the influx of immunocompetent cells to affected tissues by neutralizing the activity of at least one type of chemoattractant molecule, for example, RANTES or IL-16, that is normally released by fibroblasts and that attracts immunocompetent cells. For example, one approach is to use the information available regarding the structure and function of the targeted chemoattractant molecule to generate binding molecule populations from molecules known to function as cytokine binding molecules or known to exhibit or be capable of exhibiting binding affinity specific for the chemoattractant molecule, for example, RANTES or IL-16, such as fragments or mimetics of the CCR5 receptor found on CD4+ T cells. A modulating substance that prevents the influx of immunocompetent cells to affected tissues by neutralizing the activity of at 20l least one type of chemoattractant molecule, for example, RANTES or IL-16, can be an antibody and other receptor of the immune repertoire. The normal function of such immune receptors is to bind essentially an infinite number of different antigens and ligands. Therefore, generating a diverse population of binding molecules from an immune repertoire, for example, can be useful for identifying a modulating substance that prevents the influx of immunocompetent cells to affected tissues by neutralizing the activity of at least one type of chemoattractant molecule, for example, RANTES or IL-16.

A modulating substance that prevents the influx of immunocompetent cells to affected tissues by neutralizing the activity of at least one type of chemoattractant molecule, for example, RANTES or IL-16, can further be identified from a large population of unknown molecules by methods well known in the art and described herein. Such a population can be a random library of peptides or small molecule compounds and can be generated to contain a sufficient diversity of sequence or structure so as to contain a modulating substance that prevents the influx of immunocompetent cells to affected tissues by neutralizing the activity of at least one type of chemoattractant molecule, for example, RANTES or IL-16, or their respective nucleic acids. Those skilled in the art will know what size and diversity is necessary or sufficient for the intended purpose. A population of sufficient size and complexity can be generated so as to have a high probability of containing a modulating substance that prevents the influx of immunocompetent cells to affected tissues by neutralizing the activity of at least one type of chemoattractant molecule, for example, RANTES or IL-16, with sufficient affinity to decrease cell recruitment activity. Numerous other types of library molecule populations exist and are described further below.

Any substance that binds to a receptor, to a gene region that controls expression, or to a regulatory molecule that modulates activity or expression of the targeted chemoattractant molecule as well as any substance that binds to a regulatory molecule that modulates receptor expression of the targeted chemoattractant molecule can be an inhibitory modulating substance useful for practicing the invention. Any substance that modulates or regulates activity or expression of the targeted chemoattractant molecule, activity or expression of the corresponding receptor, a gene region that controls expression of the targeted chemoattractant molecule, or a regulatory molecule that modulates activity or expression of the targeted chemoattractant molecule as well as any regulatory molecule that modulates or regulates expression of the corresponding receptor is a modulating substance useful for practicing the invention. Thus, a substance that prevents the influx of immunocompetent cells to affected tissues by neutralizing the activity of at least one type of chemoattractant molecule, for example, RANTES or IL-16, can act directly through a binding or non-binding interaction with the chemoattractant molecule itself as well as indirectly through a binding or non-binding interaction with any other molecule that regulates or modulates expression or activity of the targeted chemoattractant molecule.

A substance can modulate the expression or activity of a targeted chemoattractant molecule sufficiently to decrease its activity is useful for practicing the claimed methods of reducing the severity of a condition associated with fibroblast mediated T-lymphocyte infiltration by preventing the influx of immunocompetent cells. In addition, such a neutralizing modulating substance can decrease activity or expression of the chemoattractant molecule by modulating a corresponding receptor, a regulatory molecule that, in turn, modulates the activity or expression of the chemoattractant molecule, or a gene region that controls expression of the chemoattractant molecule. For example, a substance useful for practicing the claimed invention can be an antibody against a regulator molecule that modulates expression or activity of the targeted chemoattractant molecule, for example, RANTES or IL-16. For example, an anti-RANTES or anti-IL-16 antibody is a useful neutralizing substance for practicing the methods of the invention. In addition, since chemoattractant molecules are secreted proteins known to bind to a specific T-cell receptor, a neutralizing substance useful for practicing the invention can be any binding polypeptide, receptor or fragment thereof of the immunoglobulin superfamily of receptors. Alternatively, it may be desired to use populations of random peptide populations to identify further substances that prevents the influx of immunocompetent cells to affected tissues by neutralizing the activity of at least one type of chemoattractant molecule, for example, RANTES or IL-16. Based on the guidance provided herein and that which is known in the art, those skilled in the art will know or can determine what type of approach and what type of neutralizing agent is appropriate for practicing the methods of the invention for reducing the severity of a of a condition associated with fibroblast mediated T-lymphocyte infiltration.

As described above for identification of a substance that inhibits the interaction between a receptor autoantigen and an endogenous immunoglobulin, a moderate sized population for identification of a substance that prevents the influx of immunocompetent cells to affected tissues by neutralizing the activity of at least one type of chemoattractant molecule, for example, RANTES or IL-16, can consist of hundreds and thousands of different molecules, for example, binding molecules, within the population whereas a large population will consist of tens of thousands and millions of different molecule species. More specifically, large and diverse populations of molecules for the identification of a substance useful for practicing the invention methods will contain any of about $10^4$, $10^5$, $10^6$, $10^7$, $10^8$, $10^9$, $10^{10}$, or more, different molecule species. One skilled in the art will know the approximate diversity of the population of molecules sufficient to identify a substance that prevents the influx of immunocompetent cells to affected tissues by neutralizing the activity of at least one type of chemoattractant molecule, for example, RANTES or IL-16.

A antibody with specific binding activity for a chemoattractant molecule, for example, RANTES or IL-16, can be raised using as an immunogen a substantially purified chemoattractant molecule, which can be prepared from natural sources or produced recombinantly, or a peptide portion of the targeted chemoattractant molecule including synthetic peptides. A non-immunogenic peptide portion of a chemoattractant molecule can be made immunogenic by coupling the hapten to a carrier molecule such bovine serum albumin (bSA) or keyhole limpet hemocyanin (KLH), or by expressing the peptide portion as a fusion protein. Various other carrier molecules and methods for coupling a hapten to a carrier molecule are well known in the art (see Harlow and Lane, supra, 1988; see, also, Hermanson, Bioconjugate Techniques, Academic Press, 1996, which is incorporated herein by reference). As described above, an antibody useful as a substance that neutralizes the activity of a chemoattractant molecule, for example, RANTES or IL-16, can also be raised against a regulatory molecule that modulates the expression or activity of the targeted chemoattractant molecule rather than against the chemoattractant molecule directly.

In one embodiment of the invention, the polynucleotides encoding IGF-1R, RANTES, IL-16, or regulatory molecules that modulate the expression or activity of these molecules, or any fragment thereof, or antisense molecules, can be used as substances useful for practicing the invention for therapeutic purposes. As an example, antisense molecules to the RANTES or IL-16 encoding nucleic acids can be used to block the transcription or translation of the mRNA. Specifically, cells can be transformed with sequences complementary to these nucleic acids. Such methods are well known in the art, and sense or antisense oligonucleotides or larger fragments, can be designed from various locations along the coding or control regions of sequences encoding, for example, a targeted chemoattractant molecule. Thus, antisense molecules may be used as substances to neutralize activity, or to achieve regulation of gene function in the methods of the invention.

The activity of a chemoattractant as well as the neutralizing activity of a substance can be confirmed by in vitro assays known in the art. For example, a chemotaxis assay can be used to evaluate the ability of defined signals to induce directional migration of a targeted cell population, for example, T-lymphocytes. The activity of RANTES or IL-16 can be neutralized with, for example, a human monoclonal antibody and the effect of this treatment on T cell migration to the site of inflammation can be determined. A hallmark of chemokine binding to a specific chemokine receptor is a change in intracellular calcium levels. Intracellular calcium in single, receptor-expressing T cells can be determined using a digital imaging system with a light-sensitive camera. Recombinant human proinflammatory molecule can be incubated with or without the candidate neutralizing substance and added to separate chambers of cells. The $[Ca2+]i$ is determined before and after stimulation.

As described herein, neutralization of a chemoattractant molecule also can be achieved by inhibiting the interaction between the chemoattractant molecule and its corresponding receptor, for example, a chemokine and a chemokine receptor; a cytokine and a cytokine receptor. The substance inhibiting the interaction between the chemoattractant molecule and its receptor can be a modified chemoattractant molecule, an antibody or fragment thereof that binds specifically to the chemoattractant molecule receptor, an antisense polynucleotide directed to a polynucleotide encoding the chemoattractant molecule, a nucleotide aptamer that affects the binding of the chemoattractant molecule to at least one chemoattractant molecule receptor, a peptide aptamer that affects the binding of the chemoattractant molecule to at least one chemoattractant molecule receptor, and a small molecule that affects the binding of the chemoattractant molecule to at least one chemoattractant molecule receptor. As an example, the substance can be a modified RANTES molecule, for example, modified by addition of an aminooxypentane (AOP) group to the beginning of the protein sequence. Modified in this fashion, AOP-RANTES retains its capacity to bind CCR5, but cannot induce any of RANTES biological activities with regard to the attraction or activation of T cells. AOP-RANTES can also displace other chemokines bound to CCR5, binding more tightly to the receptor. A chemically modified IL-16 molecule modified so as to retain its capacity to bind the CD4+ receptor, but without the capacity to induce any of IL-16 biological activities with regard to the attraction or activation of T cells also is useful for practicing the claimed methods. Furthermore, a fragment or peptidomimetic of a chemoattractant molecule that binds the target chemoattractant molecule receptor with sufficient affinity to decrease its activity is useful for practicing the claimed methods.

The term “specifically binds” is intended to mean the polypeptide will have an affinity for the target polypeptide that is measurably higher than its affinity for a non-specific interaction. A modified chemoattractant molecule, a fragment or peptidomimetic of a chemoattractant molecule, or an antibody or fragment thereof that can bind to the chemoattractant molecule receptor with low or high affinity so long as the binding is sufficient to inhibit the interaction between a chemoattractant molecule and its receptor. For example, a modified chemoattractant molecule can bind to the corresponding chemoattractant molecule receptor with a binding affinity (Kd) of about $10^{-4}$ M or less, $10^{-5}$ M or less, $10^{-6}$ M or less, about $10^{-7}$ M or less, including about $10^{-8}$ M or less, such as $10^{-9}$ M or less. Several methods for detecting or measuring polypeptide binding are known in the art.

The substances useful for practicing the methods of the invention can be formulated and administered by those skilled in the art in a manner and in an amount appropriate for the condition to be treated; the rate or amount of inflammation; the weight, gender, age and health of the individual; the biochemical nature, bioactivity, bioavailability and side effects of the particular compound; and in a manner compatible with concurrent treatment regimens. An appropriate amount and formulation for decreasing the severity of a condition associated with fibroblast mediated T-lymphocyte infiltration in humans can be extrapolated from credible animal models known in the art of the particular disorder. It is understood, that the dosage of a therapeutic substance has to be adjusted based on the binding affinity of the substance, such that a lower dose of a substance exhibiting significantly higher binding affinity can be administered compared to the dosage necessary for a substance with lower binding affinity.

The total amount of a substance can be administered as a single dose or by infusion over a relatively short period of time, or can be administered in multiple doses administered over a more prolonged period of time. Such considerations will depend on a variety of case-specific factors such as, for example, whether the disease category is characterized by acute episodes or gradual or chronic deterioration. For a individual affected with chronic deterioration, for example, as associated with neuroinflammatory disorder such as MS, the substance can be administered in a slow-release matrix, which can be implanted for systemic delivery or at the site of the target tissue. Contemplated matrices useful for controlled release of therapeutic compounds are well known in the art, and include materials such as DepoFoam™, biopolymers, micropumps, and the like.

The substances administered in the methods of the invention can be administered to the individual by any number of routes known in the art including, for example, systemically, such as intravenously or intraarterially. A therapeutic substance can be provided in the form of isolated and substantially purified polypetides and polypeptide fragments in pharmaceutically acceptable formulations using formulation methods known to those of ordinary skill in the art. These formulations can be administered by standard routes, including for example, topical, transdermal, intraperitoneal, intracranial, intracerebroventricular, intracerebral, intravaginal, intrauterine, oral, rectal or parenteral (e.g., intravenous, intraspinal, intrathecal, subcutaneous or intramuscular) routes. Intrathecal administration of a therapeutic substance into the intradural or subarachnoid space is a preferred route for practicing the methods of the invention for decreasing the severity of a neuroinflammatory condition associated with fibroblast mediated T-lymphocyte infiltration. Intravenous administration of a therapeutic substance also is a preferred route for practicing the methods of the invention. In addition, a therapeutic substance administered in the methods of the invention can be incorporated into biodegradable polymers allowing for sustained release of the substance useful for reducing the severity of a condition associated with fibroblast mediated T-lymphocyte infiltration. Biodegradable polymers and their use are described, for example, in Brem et al., *J. Neurosurg.* 74:441-446 (1991), which is incorporated herein by reference.

A therapeutic substance administered in the methods of the invention also can be administered as a solution or suspension together with a pharmaceutically acceptable medium. Such a pharmaceutically acceptable medium can include, for example, sterile aqueous solvents such as sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable medium can additionally contain physiologically acceptable compounds that act, for example, stabilize the neutralizing agent, increase its solubility, or increase its absorption. Such physiologically acceptable compounds include, for example, carbohydrates such as glucose, sucrose or dextrans; antioxidants such as ascorbic acid or glutathione; receptor mediated permeabilizers, which can be used to increase permeability of the blood-brain barrier; chelating agents such as EDTA, which disrupts microbial membranes; divalent metal ions such as calcium or magnesium; low molecular weight proteins; lipids or liposomes; or other stabilizers or excipients. Those skilled in the art understand that the choice of a pharmaceutically acceptable carrier depends on the route of administration of the compound containing the neutralizing substance and on its particular physical and chemical characteristics.

Formulations suitable for parenteral administration include aqueous and non-aqueous sterile injection solutions such as the pharmaceutically acceptable mediums described above. The solutions can additionally contain, for example, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

For applications that require the compounds and compositions to cross the blood-brain barrier, formulations that increase the lipophilicity of the compound are particularly desirable. For example, the neutralizing agent can be incorporated into liposomes (Gregoriadis, *Liposome Technology, Vols. I to III,* 2nd ed. (CRC Press, Boca Raton Fla. (1993)). Liposomes, which consist of phospholipids or other lipids, are nontoxic, physiologically acceptable and metabolizable carriers that are relatively simple to make and administer.

A therapeutic substance administered in the methods of the invention can also be prepared as nanoparticles. Adsorbing peptide compounds onto the surface of nanoparticles has proven effective in delivering peptide drugs to the brain (see Kreuter et al., *Brain Research* 674:171-174 (1995)). Exemplary nanoparticles are colloidal polymer particles of polybutylcyanoacrylate with a therapeutic substance to be administered in the methods of the invention adsorbed onto the surface and then coated with polysorbate 80.

Image-guided ultrasound delivery of a therapeutic substance administered in the methods of the invention through the blood-brain barrier to selected locations in the brain can be utilized as described in U.S. Pat. No. 5,752,515. Briefly, to deliver a therapeutic substance past the blood-brain barrier a selected location in the brain is targeted and ultrasound used to induce a change detectable by imaging in the central nervous system (CNS) tissues and/or fluids at that location. At least a portion of the brain in the vicinity of the selected location is imaged, for example, via magnetic resonance imaging (MRI), to confirm the location of the change. An therapeutic substance administered in the methods of the invention into the patient's bloodstream can be delivered to the confirmed location by applying ultrasound to effect opening of the blood-brain barrier at that location and, thereby, to induce uptake of the substance.

In addition, polypeptides called receptor mediated permeabilizers (RMP) can be used to increase the permeability of the blood-brain barrier to molecules such as therapeutic or diagnostic substances as described in U.S. Pat. Nos. 5,268,164; 5,506,206; and 5,686,416. These receptor mediated permeabilizers can be intravenously co-administered to a host with molecules whose desired destination is the cerebrospinal fluid compartment of the brain, for example, in the treatment od a autoimmune neuroinflammatory condition. The permeabilizer polypeptides or conformational analogues thereof allow therapeutic substances to penetrate the blood-brain barrier and arrive at their target destination.

In current treatment regimes for autoimmune diseases, more than one compound is often administered to an individual for management of the same or different aspects of the disease. Similarly, in the methods of the invention involving reducing the severity of a condition associated with fibroblast mediated T-lymphocyte infiltration, a therapeutic substance can advantageously be formulated with a second therapeutic compound such as an anti-inflammatory compound, immunosuppressive compound or any other compound that manages the same or different aspects of the disease. Such compounds include, for example, methylprednisolone acetate, dexamethasone and betamethasone. As an example, for treatment of Graves' disease a therapeutic substance can advantageously be formulated with a second therapeutic compound such as antithyroid drugs, including propylthiouracil (PTU) and methimazole (Tapazole®); beta-adrenergic blocking drugs, including atenolol (Tenormin®), nadolol (Corgard®), metoprolol (Lopressor®), and propranolol (Inderal®); and radioiodine.

Contemplated methods of reducing the severity of a condition associated with fibroblast mediated T-lymphocyte infiltration include administering a therapeutic substance useful in the methods of the invention alone, in combination with, or in sequence with, such other compounds. Alternatively, combination therapies can consist of fusion proteins, where the therapeutic substance useful in the methods of the invention is linked to a heterologous protein, such as a therapeutic protein.

The invention also provides a method of diagnosing or predicting the susceptibility to an autoimmune disease associated with fibroblast mediated T-lymphocyte infiltration in a individual suspected of having a such a disease by obtaining a test tissue sample of the individual; measuring the level of antibodies specific for the IGF-1 Receptor, and comparing the measured expression levels of antibodies to levels of antibodies from a control tissue sample, wherein a 2-fold or more increase of antibody levels in the test sample compared to the control sample indicates the presence of an autoimmune disease associated with fibroblast mediated T-lymphocyte infiltration.

The invention further provides method of diagnosing or predicting the susceptibility to an autoimmune disease associated with fibroblast mediated T-lymphocyte infiltration in a individual suspected of having such a disease by obtaining a test tissue sample of the individual; measuring the level of at least one type of chemoattractant molecule capable of recruiting T-lymphocytes, and comparing the measured expression levels of the chemoattractant molecule to levels from a control tissue sample, wherein a 2-fold or more increase in the measured level of the chemoattractant molecule in the test sample compared to the control sample indicates the presence of an autoimmune disease associated with fibroblast mediated T-lymphocyte infiltration.

As used herein, the term "sample" is intended to mean any biological fluid, cell, tissue, organ or portion thereof, that includes or potentially includes disease-specific auto-antibodies, for example, anti-IFG1R, or a chemoattractant molecule associated with fibroblast mediated T-lymphocyte recruitment. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or polypeptide preparation.

The diagnostic and prognostic methods of the invention are useful for determining if a patient is at risk for or afflicted with an autoimmune disease associated with fibroblast mediated T-lymphocyte infiltration in an individual. The diagnostic and prognostic methods of the invention can be used to identify individuals likely to experience an autoimmune disease associated with fibroblast mediated T-lymphocyte infiltration in an individual so that suitable therapies can be offered.

Autoimmune disease associated with fibroblast mediated T-lymphocyte infiltration include, for example, Graves' Disease and the Rheumatoid Arthritis. As described herein, based on the existence of trauma-induced autoimmunity by which the autoreactive repertoire regulates ongoing central nervous system (CNS) immunologic responses, the diagnostic and predictive methods of the invention also are applicable in the context of CNS trauma and neurodegenerative diseases. The methods herein are applicable for the diagnosis or treatment of any or all conditions associated with fibroblast mediated T-lymphocyte infiltration.

The invention provides a method of diagnosing or predicting an autoimmune condition based on the finding of a positive correlation between the expression of auto-antibodies directed against the IFG1 Receptor on fibroblasts cells and the degree or extent of the condition associated with fibroblast mediated T-lymphocyte infiltration. The diagnostic methods of the invention are applicable to numerous conditions and pathologies as described above. One consequence of progression into these conditions is an increased expression of IgGs that specifically bind to the IGF-1 Receptor, which serves as the autoantigen. This increase in anti-IGF-1R antibody expression in individuals suffering from a condition associated with fibroblast mediated T-lymphocyte infiltration can be measured by comparing the amount or concentration of anti-IGF-1R antibody to that found, for example, in normal blood, lymph or tissue samples, for example, lymph node samples. A two-fold or more increase in anti-IGF-1R antibody expression in a test sample relative to samples obtained from control tissue sample is indicative of a condition associated with fibroblast mediated T-lymphocyte infiltration. Similarly, an increase in anti-IGF-1R antibody expression leading to two-fold or more secretion into the blood or other circulatory fluids of the individual compared to normal blood or fluid samples also is indicative of a condition associated with fibroblast mediated T-lymphocyte infiltration.

As a diagnostic indicator, anti-IGF-1R antibodies can be used qualitatively to positively identify a condition associated with fibroblast mediated T-lymphocyte infiltration as described above. Alternatively, anti-IGF-1R antibodies also can be used quantitatively to determine the degree of or susceptibility to a condition associated with fibroblast mediated T-lymphocyte infiltration. For example, successive increases in the expression levels, including levels of anti-IGF-1R antibodies in circulating fluids, can be used as a predictive indicator of the degree or severity of a condition associated with fibroblast mediated T-lymphocyte infiltration, for example, Graves' disease or Rheumatoid Arthritis, because increased expression, leading to a rise in accumulated levels, for example, also can positively correlate with increased severity of such a condition. The higher the level of auto-antibody expression, the later the stage of the condition associated with fibroblast mediated T-lymphocyte infiltration. Disease-specific auto-antibodies and chemoattractant molecules associated with fibroblast-mediated T-lymphocyte infiltration also can be used quantitatively to distinguish between distinguish between the different types of autoimmune conditions.

Correlative increases can be determined by comparison of disease-specific auto-antibodies or chemoattractant molecules associated with fibroblast-mediated T-lymphocyte infiltration from the individual having, or suspected of having a particular condition to corresponding expression levels from known samples determined to exhibit the particular condition. Alternatively, correlative increases also can be determined by comparison of disease-specific autoantibodies or chemoattractant molecules associated with fibroblast-mediated T-lymphocyte infiltration expression from the test individual in combination with expression levels of other known markers of a particular condition such as, for example, thyrotropin, antibodies directed against the Thyrotropin receptor (anti-TSH-R antibodies), or thyroid hormone levels in Graves' patients; SR proteins or anti-SR autoantibody levels for systemic lupus erythematosus (see Neugebauer et al., *Arthritis Rheum.* 43(8):1768-78 (2000)). Similarly, other known markers associated with particular autoimmune disorders can be used, for example, as an internal or external standard for correlation of stage-specific expression with increases in the expression of other known markers associated with a condition associated with fibroblast mediated T-lymphocyte infiltration. Conversely, a regression in the severity of a condition or pathology can be followed by a corresponding decrease in disease-specific auto-antibodies or chemoattractant molecules expression levels and can similarly be assessed using the methods described above.

Given the teachings and guidance provided herein, those skilled in the art will know or can determine the stage or severity of a particular condition associated with fibroblast mediated T-lymphocyte infiltration based on a determination of disease-specific auto-antibody or chemoattractant molecule expression and using known procedures and marker comparisons other than those described above. For a review of recognized values for such other marker in normal versus pathological tissues, see for example, Endocrinology (Degroot and Jameson, Eds., 4th ed., 2001, W B Saunders, Philadelphia); Werner and Ingbar's the Thyroid: A Fundamental and Clinical Text (braverman and Utiger, Eds., $7^{th}$ ed., 1996, Lippincott, Philadelphia), both of which are incorporated herein by reference in their entirety.

Therefore, the invention provides a method for both diagnosing and prognosing a condition associated with fibroblast mediated T-lymphocyte infiltration, for example, Graves' disease (GD) and Rheumatoid Arthritis (RA) as well as other autoimmune conditions.

The use of disease-specific auto-antibody or chemoattractant molecule expression levels in tissue samples or samples obtained from the circulatory system as a diagnostic indicator of a condition associated with fibroblast mediated T-lymphocyte infiltration allows for early diagnosis as a predictive indicator when no physiological or pathological symptoms are apparent. The methods are applicable to any individuals suspected of being afflicted with or at risk for an autoimmune disease, for example, women in their childbearing years with a family history of autoimmune disorders. In this regard, it is known that about 75 percent of autoimmune diseases occur in women, most often during their childbearing years. A genetic component of autoimmune diseases is suspected, since multiple family members may be affected, although not always with the same disease. For Graves' disease, studies have shown that 75% of monozygotic twins are discordant for the disease. Because the severity of the disease can change after pregnancy or menopause, hormones also are suspected to play a role. In addition, onset may follow viral or bacterial infections suggesting that autoimmune diseases can be triggered by certain pathogens that ultimately cause an abnormal immune response against the body.

Taking into account the above-cited and other art known risk factors, the diagnostic methods of the invention are applicable to individuals predicted to be at risk for a condition associated with fibroblast mediated T-lymphocyte infiltration prior to onset of overt clinical symptoms. By determining the expression levels of a disease-specific auto-antibody, for example, anti-IGF-1R antibody, or a chemoattractant molecule, for example, RANTES or IL-16, in tissue test samples or test samples obtained from the circulatory system and comparing the measured level to that of an appropriate control sample, it is possible to determine whether there is an increase in these levels in the individual suspected of having a condition associated with fibroblast mediated T-lymphocyte infiltration compared to normal individuals. Those skilled in the art will know by using routine examinations and practices in the field of medicine those individuals who are candidates for diagnosis by the methods of the invention.

For example, individuals suspected of having a particular autoimmune condition associated with fibroblast mediated T-lymphocyte infiltration can be identified by exhibiting presenting signs of the particular condition which are known in the art and depend on the specific disease and the organ or tissue that is affected, but generally can include, for example, low-grade fever, malaise and fatigue. Prognostic methods of this invention also are applicable to individuals after diagnosis of a condition associated with fibroblast mediated T-lymphocyte infiltration, for example, to monitor improvements or identify a remission.

Therefore, the invention provides a method of predicting the onset of a condition associated with fibroblast mediated T-lymphocyte infiltration. The method consists of determining increased expression levels of a disease-specific auto-antibody, for example, anti-IGF-1R antibody, or a chemoattractant molecule, for example, RANTES or IL-16, in a test 4 sample from an individual having or suspected of having a condition associated with fibroblast mediated T-lymphocyte infiltration and comparing the measured expression level to a control sample isolated from a normal individual, where an increased expression level of a disease-specific auto-antibody, for example, anti-IGF-1R antibody, or a chemoattractant molecule, for example, RANTES or IL-16, in the sample indicates the onset of a condition associated with fibroblast mediated T-lymphocyte infiltration.

The diagnostic methods of the invention are applicable for use with a variety of different types of samples isolated or obtained from an individual having, or suspected of having a condition associated with fibroblast mediated T-lymphocyte infiltration. For example, samples applicable for use in one or more diagnostic formats of the invention, include tissue and cell samples. A tissue or cell sample can be obtained, for example, by biopsy or surgery. As described below, and depending on the format of the method, the tissue can be used whole or can be disassociated into smaller pieces, cell aggregates or individual cells. When measuring polypeptide or activity levels, amplification of the signal with enzymatic coupling or photometric enhancement can be employed using only a few or a small number of cells. Whole tissue obtained from a biopsy of, for example, a lymph node is one example of a cell sample. Of particular interest for practicing the invention methods, fibroblast strains, for example, orbital fibroblasts can be initiated from surgical waste. Dermal fibroblasts can be derived, for example, from punch biopsies or obtained from a third-party source, for example, the American Type Culture Collection (ATCC). Whole tissue cell samples can be assayed employing any of the formats described below.

Individual cells and cell aggregates from an individual having, or suspected of having a particular condition associated with fibroblast mediated T lymphocyte infiltration is another example of a cell sample which can be analyzed for increased expression of polypeptide or activity. The tissue or cell sample can be obtained directly from the individual or, alternatively, it can be obtained from other sources for testing. Similarly, the cell sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the diagnostic methods of the invention is that they do not require histological analysis of the sample. As such, the sample can be initially disaggregated, lysed, fractionated or purified and the active component stored for later diagnosis.

Fluid samples that can be measured for expression levels of, for example, a disease-specific immunoglobulin or autoantibody, autoantigen, chemoattractant molecule, include, for example, blood, serum and lymph. Other bodily fluids are known to those skilled in the art and are similarly applicable for use as a sample in the diagnostic methods of the invention. One advantage of analyzing fluid samples is that they are readily obtainable, in sufficient quantity, without invasive procedures as required by biopsy and surgery. Analysis of fluid samples such as blood, serum and lymph will generally be in the diagnostic formats described above and below which measure levels or activity. As the polypeptide is circulating, the methods will be similar to those which measure expression levels from cell lysates, fractionated portions thereof or purified components.

A suitable control for comparison can be a sample obtained from a donor individual known not to have the particular condition targeted by the diagnostic or prognostic method. The control sample for comparison can be measured simultaneously with one or more test samples or, alternatively, expression levels can be established for a particular type of sample and standardized to internal or external parameters such as protein content, cell number or mass of tissue. Such standardized control samples can then be directly compared with results obtained from the test sample. An increase of two-fold or more of, for example, a disease-specific immunoglobulin or autoantibody, autoantigen, chemoattractant molecule, expression levels indicates the presence of the particular condition in the tested individual.

The diagnostic procedures described above and below can additionally be used in conjunction with other biomarkers, such as, for example, anti-TSHR-antibodies in the case of Graves' disease (GD), for simultaneous or independent corroboration of a sample. Those skilled in the art will know which markers are applicable for use in conjunction with a particular condition to delineate more specific diagnostic information such as that described above.

Therefore, the invention provides a method of diagnosing or predicting the susceptibility to an autoimmune disease associated with fibroblast mediated T-lymphocyte infiltration in an individual suspected of having such a disease by obtaining a test tissue sample of the individual; measuring the level of at least one type of chemoattractant molecule capable of recruiting T-lymphocytes, and comparing the measured expression levels of the type of chemoattractant molecule to levels of chemoattractant molecules from a control tissue sample. A 2-fold or more increase in the measured level of the type of chemoattractant molecule in the test sample compared to the control sample indicates the presence of an autoimmune disease associated with fibroblast mediated T-lymphocyte infiltration. Further as described herein, the invention provides a method of diagnosing or predicting the susceptibility to an autoimmune disease associated with fibroblast mediated T-lymphocyte infiltration in an individual suspected of having such a disease associated with fibroblast mediated T-lymphocyte infiltration by obtaining a test tissue sample of the individual; measuring the level of antibodies specific for the IGF-1 Receptor, and comparing the measured expression levels of antibodies to levels of antibodies from a control tissue sample, wherein a 2-fold or more increase of antibody levels in the test sample compared to the control sample of antibodies indicates the presence of an autoimmune disease associated with fibroblast mediated T-lymphocyte infiltration.

In a further embodiment, the invention provides a method of identifying a substance that modulates fibroblast mediated T-lymphocyte infiltration by inducing fibroblast mediated T-lymphocyte infiltration in a population of cells; contacting a first sub-population of the cells with a testsubstance, and a second sub-population of the cells with a control-substance; and comparing the amount of fibroblast mediated T-lymphocyte infiltration between the first and second sub-populations of cells, wherein a difference in the amount of fibroblast mediated T-lymphocyte infiltration between the first and second sub-populations of cells indicates that the testsubstance modulates fibroblast mediated T-lymphocyte infiltration.

In a related embodiment, the invention provides a method of identifying a substance capable of modulating the interaction between an IGF-1-Receptor and an endogenous immunoglobulin by contacting a sample containing the IGF-1-Receptor and an endogenous immunoglobulin with a test substance under conditions that allow for the interaction between the IGF-1-Receptor and the endogenous immunoglobulin, and measuring the interaction between the IGF-1-Receptor and the endogenous immunoglobulin, wherein a decrease in the amount of interaction between the IGF-1-Receptor and the endogenous immunoglobulin in the presence of the test substance compared to the absence of the test substance indicates that the substance is capable of modulating the interaction between the IGF-1-Receptor and the endogenous immunoglobulin.

A substance capable of modulating the interaction between an IGF-1-Receptor and an endogenous immunoglobulin can decrease the amount of interaction. Such a substance is useful in the therapeutic embodiments of the invention directed to reducing the severity of a condition associated with fibroblast mediated T-lymphocyte infiltration.

The invention also provides a method of identifying a substance capable of inhibiting the release of at least one type of chemoattractant molecule from fibroblasts by contacting a fibroblast cell sample with a test substance under conditions that are associated with the release of the chemoattractant, and measuring the amount of the chemottractant that is released from the fibroblast cell sample, wherein a decrease in the amount of the chemottractant that is released from the sample in the presence of the test substance compared to the absence of the test substance indicates that the substance is capable of inhibiting the release of the type of chemottractant molecule from fibroblasts. The fibroblast cell sample can be contacted with a control substance under conditions that are associated with the release of said type of chemoattractant molecule, for example, a chemokine such as the C-C chemokine RANTES or a cytokine such as the specific CD4+ ligand IL-16. For example, the fibroblast cell sample can be contacted with disease-specific antibodies that are known to specifically bind and activate an autoantigen receptor resulting in the subsequent release of a chemoattractant molecule that recruits immunocompetent cells. In addition, as described in Example IV, induction of IL-16 expression and release of this chemoattractant molecule from fibroblasts involves the FRAP/mTOR pathway and activation of the serine/threonine kinase $p70^{s6k}$. This pathway can be inhibited by the macrolide rapamycin as described by Brennan et al., *Mol. Cell. Biol.* 19:4729 (1999), which is incorported herein by reference.

Thus, rapamycin is a modulating substance that can prevent the release by a fibroblasts of a chemoattractant molecule. Similarly, the release of the chemoattractant molecule IL-16 from fibroblasts is caspase-3 dependent (Example III) such that a caspase-3 inhibitor is a further modulating substance that can prevent the release by a fibroblasts of a chemoattractant molecule.

As described herein, a substance capable of inhibiting the release of at least one type of chemoattractant molecule from fibroblasts represents a modulating substance useful in the therapeutic embodiments of the invention directed to reducing the severity of a condition associated with fibroblast mediated T-lymphocyte infiltration. A suitable test sample can be a fibroblast cell sample obtained from an individual afflicted with an autoimmune disease associated with fibroblast mediated T-lymphocyte infiltration. A suitable fibroblast test sample can contain cells that express the autoantigen and can be obtained, for example, by punch biopsy from the dermis or from a site of tissue remodeling, of an individual known to be afflicted with a condition associated with fibroblast-mediated T lymphocyte infiltration. Those skilled in the art will appreciate that, in the methods described herein, the absence of a test substance can represent the presence of a control substance.

In order to confirm the modulatory activity of a test substance it is necessary to induce the conditions that are associated with fibroblast mediated T-lymphocyte infiltration. Such a condition can be induced, for example, by exposing the fibroblast test and control samples to an immunoglobulin obtained from an individual afflicted with an autoimmune disease associated with fibroblast mediated T-lymphocyte infiltration, for example, Graves' disease (GD); a manifestation of Graves' disease (GD) associated with connective tissue remodeling such Thyroid-associated opthalmopathy (TAO) and dermopathy; Rheumatoid Arthritis; or a condition associated with neuroinflammation.

Fibroblast mediated T-lymphocyte infiltration can be induced in a variety of ways. Any compound or process that results in fibroblast mediated T-lymphocyte infiltration can be used to induce this process in the methods of the invention. For example, compounds that mimic the endogenous anti-IFG1R immunoglobulin or a chemoattractant molecule that is naturally released by fibroblasts to attract T-lymphocytes can be used in the screening methods of the invention. Induction of fibroblast mediated T-lymphocyte infiltration can occur through activation of IFG1R or through other mechanisms. Likewise, activation of IFG1R can occur through the binding of an endogenous immunoglobulin or a different compound. For example, a truncated form of an anti-IFG1R immunoglobulin that retains the ability to bind to the IGF-1R and lead to fibroblast activation can induce fibroblast mediated T-lymphocyte infiltration.

It is understood that a fragment of an endogenous immunoglobulin that recognizes IFG1R can be sufficient in order to induce the conditions that are associated with fibroblast mediated T-lymphocyte infiltration. For example, a fragment of an endogenous immunoglobulin that retains substantially the same ability to specifically bind to IFG1R as the entire polypeptide is useful for practicing the invention methods. A fragment of a chemoattractant molecule that recognizes its corresponding receptor can similarly be sufficient to produce the conditions that are associated with fibroblast mediated T-lymphocyte infiltration. Fragments can include, for example, amino terminal, carboxyl terminal, or internal deletions of a full length substance chemottractant molecule. For example, a fragment can contain at least about 50, 100, 150, 200, 250, 300, 350, 400, or more contiguous or non-contiguous amino acid residues of a full-length polypeptide. Polypeptide fragments can be generated, for example, using recombinant DNA methods or enzymatic or chemical cleavage of larger polypeptides. In addition, various molecules, such as other polypeptides, carbohydrates, or lipids, or small molecules can be attached to a chemoattractant molecule or an endogenous immunoglobulin including fragments of these molecules. For example, a label moiety can be attached to a chemottratractant molecule.

It is understood that limited modifications can be made to an antibody without destroying its specific binding activity with regard to, for example, an autoantigen such as IFG1R. Various modifications of the primary amino acid sequence can result in polypeptides having substantially equivalent, decreased, or enhanced function as compared to the endogenous immunoglobulin. Those skilled in the art recognize that such modifications can be desirable at times in order to enhance the bioactivity, bioavailability or stability of a polypeptide, or to facilitate its synthesis or purification. Contemplated amino acid substitutions to the native sequence of a polypeptide can include, for example, conservative changes, wherein a substitutive amino acid has similar structural or chemical properties, for example, replacement of a polar amino acid with another polar amino acid or replacement of a charged amino acid with a similarly charged amino acid. Those skilled in the art also recognize that non-conservative changes, for example, replacement of an uncharged polar amino acid with a non-polar amino acid or replacement of a charged amino acid with an uncharged polar amino acid can also be made without affecting a function of a polypeptide such as an anti-IFG1R antibody or a chemottractant molecule. In addition, a variety of polypeptide modifications are known in the art for constraining the structure of polypeptides to enhance stability or binding (Cabezas and Satterthwait, supra, 1999; Stanfield et al., supra, 1999).

Cells used in the screening methods of the invention can include primary cells as well as cell lines. Primary cells in a tissue section or grown in cell culture can be used in the invention. For example, human fibroblasts can be used in the methods of the invention and can be grown in cell culture either in an isolated form or with other cells that can be used to provide better growth of the fibroblasts. In addition, the fibroblasts can be used in the invention as a tissue slice, for example, a lymph node tissue slice that is used directly after isolation or that has been maintained in tissue culture. Cell and tissue culture techniques are well known in the art.

Cell lines can also be used in the methods of the invention. Several neuronal and non-neuronal cell lines have been established and are well known in the art. Appropriate cell lines are available from the American Type Culture Collection (ATCC) or from individual investigators. In addition, cells can be isolated from an individual afflicted with a particular disease and immortalized by methods well known in the art. Non-fibroblast cell lines can be used in the invention, for example, any cell line that can be transfected with IFG1R. Non-neuronal cell lines that can be transfected include, for example, 293T, HeLa, COS-7, and Jurkat cells, among others. Transfection techniques, such as calcium phosphate, lipids, and electroporation are well known in the art. Furthermore, stem cells or other pluripotent cells can be used in the invention. These cells can be used either as primary cells or cell lines in either an undifferentiated or differentiated state.

The level of fibroblast mediated T-lymphocyte infiltration can be measured by any of a variety of methods known to one skilled in the art. For example, a chemotaxis assay can be used to evaluate the directional migration of T-lymphocytes. Once fibroblast mediated T-lymphocyte infiltration has been induced in a cell, the invention methods contemplate contacting the cell with a test-substance to identify a substance that modulates fibroblast mediated T-lymphocyte infiltration. The methods provided by the invention are particularly useful to identify, from among a diverse population of molecules, those substances that modulate fibroblast mediated T-lymphocyte infiltration. Methods for producing libraries containing diverse populations of molecules, including chemical or biological molecules such as simple or complex organic molecules, peptides, proteins, peptidomimetics, glycoproteins, lipoproteins, polynucleotides, and the like, are well known in the art (Huse, U.S. Pat. No. 5,264,563; Blondelle et al., *Trends Anal. Chem.* 14:83-92 (1995); York et al., *Science* 274:1520-1522 (1996); Gold et al., *Proc. Natl. Acad. Sci., USA* 94:59-64 (1997); Gold, U.S. Pat. No. 5,270,163). Such libraries also can be obtained from commercial sources.

Since libraries of diverse molecules can contain as many as $10^{14}$ to $10^{15}$ different molecules, a screening assay of the invention provides a simple means for identifying those substances in the library that can modulate fibroblast mediated T-lymphocyte infiltration. In particular, a screening assay of the invention can be automated, which allows for high through-put screening of randomly designed libraries of agents to identify those particular agents that can modulate fibroblast mediated T-lymphocyte infiltration.

A screening assay can assay two or more samples simultaneously in order to identify a substance with the desired activity. Several formats are available for screening which can allow for a low number or high number of samples to be screened simultaneously. For example, 10, 100, 1000, 10,000, 100,000, 1,000,000 or more compounds can be assayed simultaneously using low or high thorough-put formats. Screening assays often utilize isolated cells or tissues but can also use a cell free system such as a chemical or biological solution or a cell free extract derived from cells. In addition, a screening assay could utilize whole organisms or animals. As understood by one skilled in the art, the particular design of a screening assay depends on the desired activity of the compound one is seeking and the available reagents.

As described below, substance that modulates fibroblast mediated T-lymphocyte infiltration can be a compound or molecule that binds IFG1R or any other molecule with sufficient affinity to modulate fibroblast mediated T-lymphocyte infiltration and can be a macromolecule, such as polypeptide, nucleic acid, carbohydrate or lipid. Thus, a substance that modulates fibroblast mediated T-lymphocyte infiltration can be an antibody, antisense nucleic acid and any compound identified by the methods described below. A substance that modulates fibroblast mediated T-lymphocyte infiltration can also be a derivative, analogue or mimetic compound as well as a small organic compound as long as fibroblast mediated T-lymphocyte infiltration is modulated in the presence of the compound. The size of a substance that modulates fibroblast mediated T-lymphocyte infiltration compound is not important so long as the molecule exhibits or can be made to exhibit such modulating activity. For example, a substance that modulates fibroblast mediated T-lymphocyte infiltration can be as little as between about one and six, and as large as tens or hundreds of monomer building blocks which constitute a macromolecule or chemical binding molecule. Similarly, an organic compound can be a simple or complex structure so long as it has sufficient activity.

A substance that modulates fibroblast mediated T-lymphocyte infiltration can be incorporated in a therapeutic formulation that increases target specificity. For example, a particular cell type, for example, fibroblast, monocyte or macrophage, may express a unique cell surface marker, cell surface receptor or a ligand for a particular receptor. In such a case, an antibody, for example, a disease specific IgG, can be raised against the unique cell surface marker and a modulating substance can be linked to the antibody. Upon administration of the drug/antibody complex to the patient, the binding of the antibody to the cell surface marker results in the targeted delivery of a relatively high concentration of the substance. The modulating substance also can be linked to the specific ligand or to the receptor, respectively, thus providing a means to target a relatively high concentration.

Various cell types can express unique markers and, therefore, provide potential targets for homing molecules that can target a modulating substance of the invention to a desired cell type, for example, fibroblasts.

Those skilled in the art know how to identify specific target cell markers that are expressed in only one or a few tissues or and to identify molecules that specifically interact with such markers. Various cell types can express unique markers and, therefore, provide potential targets for homing molecules. Methods are now available for producing large populations of molecules and for screening libraries of molecules to identify those of interest, for example, phage peptide display libraries can be used to express large numbers of peptides that can be screened in vitro with a particular target molecule or a cell of interest in order to identify peptides that specifically bind a target molecule or cell. Screening of such phage display libraries has been used, for example, to identify ligands that specifically bind various antibodies and cell surface receptors. Screening of a phage display library generally involves in vitro panning of the library using a purified target molecule. Phage that bind the target molecule can be recovered, individual phage can be cloned and the peptide expressed by a cloned phage can be determined. Such a peptide can be useful for delivery of a substance linked to the peptide to cells expressing the target molecule, for example, fibroblasts.

It is understood that modifications which do not substantially affect the activity of the various embodiments of this invention are also included within the definition of the invention provided herein. Accordingly, the following examples are intended to illustrate but not limit the present invention.

EXAMPLE I

Graves' Disease Serum Elicits IqG-mediated Release of Chemoattractant Molecules from Activated Fibroblasts This example demonstrates that serum from patients with Graves' disease elicits IgG-mediated release of lymphocyte chemoattraction activity from fibroblasts.

Human fibroblasts derived from patients with Graves' disease and from normal donors that are maintained under basal culture conditions release very low levels of chemoattractant activity when the conditioned medium in which they are incubated is subjected to cell migration assays using NWNA-T lymphocytes as the targets.

Briefly, the results described herein were obtained utilizing human fibroblasts from individuals with Graves' disease or from donors without known thyroid disease. Orbital fibroblast strains were initiated from surgical waste. Dermal fibroblasts were derived from punch biopsies of normal appearing skin or were purchased from American Type Tissue Collection (Rockville, Md.). All patients were thought to be euthyroid at the time of tissue donation. Sera were collected from patients with Graves' disease, either without or with clinically apparent TAO and from individuals without thyroid disease (controls). These included adult men and women. The diagnosis of Graves' disease was made on clinical grounds, including suppressed TSH, elevated serum T4 levels, the presence of anti-thyroid antibodies, goiter, and typical symptoms and signs of thyrotoxicosis. Most of the individuals were euthyroid at the time of blood drawing, while few were hyperthyroid. IgG was prepared by the method previously described using protein A as described by Hardy, *Purification and Characterization of Monoclonal Antibodies* in Handbook of Experimental Immunology, Volume I, Immunochemistry (D. M. Weir, ed., Oxford: Blackwell Scientific, 1986). Fibroblast monolayers were covered with Eagle's medium supplemented with 10% FBS, antibiotics and glutamine as described by Smith, *J. Clin. Invest.* 74:2157 (1984). The cultures were incubated in a 37° C., humidified, 5% $CO_2$ atmosphere, and were serially passaged with gentle treatment with trypsin/EDTA. Fibroblast strains were utilized between the third and twelfth passage. They have been shown to not express Factor VIII or smooth muscle-specific actin (Smith et al., *J. Clin. Endocrinol. Metab.* 80:2620 (1995). There were no differences in the morphology of cultures from normal controls and patients with Graves' disease.

As shown in the upper panel of FIG. 1, when unfractionated serum from a patient with Graves' disease is added to the culture medium to a final concentration of 1% covering fibroblast monolayers, in this case from orbit, subcutaneous connective tissue, and thyroid derived from a single donor, and incubated for 24 hours, T lymphocyte chemoattractive activity is dramatically increased. A substantial fraction of the up-regulated chemotaxis can be blocked by anti-IL-16 monoclonal antibody (white column) (5 g/ml) added to the migration assay. The black column represents chemotaxis in the absence of the anti-IL-16 monoclonal antibody. Migration of 0.135% was significant at a 5% confidence limit.

Briefly, for the various chemotaxis assays described herein, fibroblasts were plated in 24-well plates and were allowed to proliferate to confluence. After rinsing the monolayers with phosphate buffered saline (PBS), cultures were shifted to medium containing 1% FBS overnight before addition of nothing (control), IL-1β (10 ng/ml), human serum (final concentration 1%) or protein A-purified human IgG to the medium. Cultures were incubated for the times indicated in the text and figure legends. At the end of these incubations, culture medium was collected quantitatively and stored at −800 C. until assayed.

Chemotaxis was assessed in a modified Boyden chemotaxis chamber utilizing human NWNA-T lymphocytes as the cellular targets, as described previously (30). Briefly, 50 μl of a cell suspension (107 cells/ml) were placed in the upper compartments of 48-well micro-chemotaxis chambers separated from 32 μl of samples by 8 μm micropore nitrocellulose filters (Neuroprobe, Cabin John, MD)and subsequently incubated at 370 C. in 5% CO2 environment for 3 hours. Filters were fixed, stained with hematoxylin, dehydrated and mounted on glass slides, and viewed under light microscopy. Lymphocyte migration was quantified by counting the total number of cells migrating beyond a certain depth, set routinely to identify a baseline migration under control conditions of 10 to 15 cells per high power field. Five high power fields were counted in duplicate for each sample and the means and standard deviations were calculated and expressed as percentage values of baseline cell migration in control buffer alone (100%). For each set of experimental conditions, at least three separate experiments were performed and the differences between experimental and control conditions were analyzed by the Student t-test using the absolute values obtained for lymphocyte migration with statistical significance accepted at the 5% level of confidence.

To assess the chemoattractant activity attributable to IL-16, neutralizing experiments were conducted by incubating culture supernatants for 15 minutes with affinity purified anti-IL-16 mAb (clone 14.1, 10 μg/ml, which neutralizes the chemoattractant activity of 50 ng/ml rIL-16). The affinity purified polyclonal rabbit anti-rIL-16 Ab was prepared from rIL-16 immunized rabbit sera as described by Cruikshank et al. *Proc. Natl. Acad. Sci. USA* 91:5109 (1994). To determine the RANTES-dependent fraction, anti-RANTES mAb (5 μg/ml, possessing an ND50 of 200 ng/ml for rRANTES) was added to the migration assay. An ELISA assay for RANTES was purchased from BioSource and neutralizing anti-RANTES antibodies were purchased from R&D Systems (Minneapolis, Minn.).

Also shown in FIG. 1 (lower panel), when fibroblast medium from Graves' disease serum-treated fibroblasts was subjected to a specific IL-16 ELISA, levels of the chemoattractant were found to be greatly elevated. IL-16 was undetectable in control cultures.

Briefly, results described herein that involve the quantitation of IL-16 protein released from the fibroblast monolayers were obtained by subjecting aliquots of conditioned medium to a specific ELISA assay, performed as described by Sciaky et al., *J. Immunol.* 164:3806 (2000). Samples from each culture were assayed in duplicate and rIL-16 and aliquots of conditioned medium were diluted in PBS to the desired concentrations. Samples of culture medium (100 μl) were incubated in a 96-well microtiter plate (Nunc, Naperville, Ill.) at 37° C. for 1 hr. Subsequent maneuvers were performed at room temperature.

Figure 2:
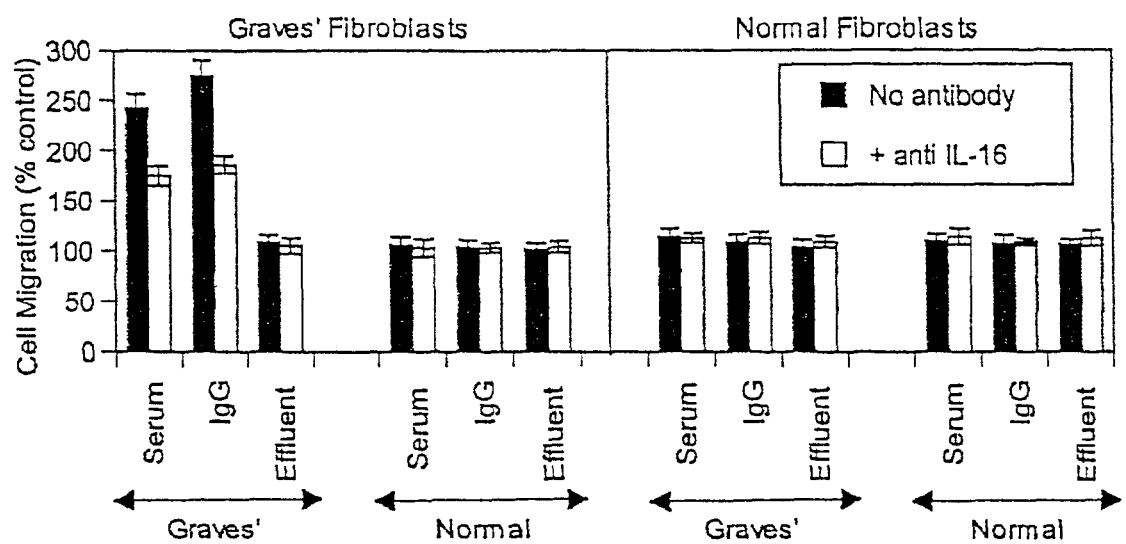
FIG. 2 shows that the induction of T cell chemotactic activity in fibroblasts by Graves' disease serum is attributable to IgG and specific to donors with Graves' disease.

As shown in FIG. 2, IL-16 inducing activity was completely adsorbed from Graves' disease sera when they were subjected to protein A column chromatography. The effluent failed to influence T cell migration. As described above, normal and Graves' disease orbital fibroblasts were treated for 24 h with serum (1%), IgG fraction (100 ng/ml) or effluent from protein A chromatography. Media were subjected to the T cell chemotaxis assay in the absence or presence of anti-IL-16 neutralizing antibody (5 μg/ml). The data are expressed as the means ±SD of three independent determinations. T cell migration greater than 135% was significant at the 5% confidence limit.

FIG. 2 also demonstrates the absence of a GD-IgG effect in fibroblasts from a donor without known thyroid disease. Moreover, IgG from a control donor failed to provoke T cell migration activity in Graves' disease or normal fibroblasts. IgG preparations from 26 different patients with Graves' disease at a final concentration of 100 ng/ml were tested in a single Graves' disease-derived fibroblast strain for their ability-to induce IL-16-dependent T cell migration and IL-16 protein. Twelve of the IgG samples were derived from individuals with Graves' disease but without obvious TAO. Twenty-five of these IgG preparations elicited an up-regulation of IL-16-dependent T cell migration. Moreover, the same GD-IgG preparations up-regulated IL-16 synthesis and release into the culture medium.

Figure 3:
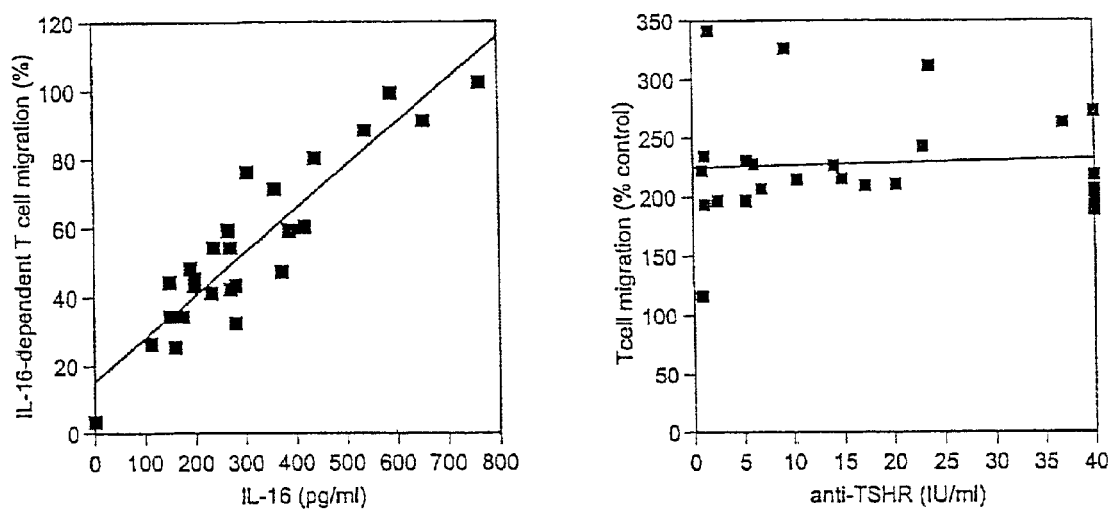
FIG. 3 shows the relationship (A) between IL-16-dependent T chemotaxis and IL-16 protein levels provoked by the treatment of Graves' disease fibroblasts with GD-IgG; and (B) between T cell chemotaxis activity provoked in Graves' disease fibroblasts by GD-IgG and serum levels of anti-TSH receptor antibody.

As shown in the left panel of FIG. 3, a high degree of correlation was found between the up-regulation of IL-16-dependent T cell migration and IL-16 protein concentrations as determined by ELISA. In contrast, sera and IgG from 12 of 13 individuals without known thyroid disease failed to increase the production of lymphocyte chemoattraction activity in, fibroblasts or detectable IL-16 protein. Briefly, culture wells with confluent Graves' disease fibroblast monolayers were treated for 24 h with GD-IgG, the media were collected and subjected to the T cell chemotaxis assay or to the IL-16 ELISA, both as described above. All samples were assayed in triplicate.

IL-16-dependent migration represents the difference between T cell chemotaxis in the presence and absence of neutralizing antibodies. The data were subjected to linear regression analysis using the equation: f(x)=0.1256108X+15.37059. (r=0.914, p=0.001). IgG preparations from 2 individuals with active rheumatoid arthritis and 2 patients with systemic lupus erythematosus failed to induce IL-16 in fibroblasts from patients with Graves' disease. These results demonstrate the specificity with regard to the type of autoimmune disease affecting the donor of IgG.

GD-IgG might be ligating the TSHR and, through that potential interaction, initiating the events culminating in the induction of IL-16. The receptor is expressed on fibroblasts from several anatomic regions and is competent to signal through $p70^{s6k}$ (Bell et al., *Am. J. Physiol.* 279:C335 (2000)). Consequently, Graves' disease fibroblasts were incubated with high concentrations of rTSH (up to 10 mU/ml)) and it was determined that the hormone fails to induce T cell chemoattractant activity or detectable IL-16 protein synthesis by Graves' disease fibroblasts. As shown in the right panel of FIG. 3, no correlation exists between GD-IgG provoked T cell migration activity (IL-16-dependent plus IL-16-independent) from immunoglobulin-treated fibroblasts and respective concentrations of anti-TSHR antibodies (TRAb). Briefly, aliquots of sera from 26 different donors with Graves' disease were subjected to IgG preparation with protein A and were subjected to T cell migration assays (ordinate) or were subjected to a radio-receptor assay for TRAb, as indicated along the abscissa.(r=0.065, p=0.62). The radio-receptor assay kit (DYNOtest-TRAK) for determining TSHR antibodies was purchased from Brahms (Hennigsdorf, Germany)and used according to the manufacturer's instructions. These findings suggest strongly that the T cell chemotaxis and IL-16 inductions provoked by GD-IgG are not related to the anti-TSHR activity present in Graves' disease sera and that the TSHR is not mediating the up-regulation by GD-IgG of IL-16.

A panel of 11 different fibroblast strains from patients with Graves' disease and 5 from individuals without known thyroid disease were challenged with GD-IgG (100 ng/ml), normal IgG (100 ng/ml) or IL-1β (10 ng/ml) (bioSource, Camarillo, Calif.) for 24 h and assessed for T cell migration activity via a lymphocyte chemotaxis assay and IL-16 production (FIG. 15). The normal and GD-IgGs used in that survey each derived from either of 2 individual donors. These were not pooled. GD-IgG induced IL-16 dependent cell migration in 10 of the Graves' disease fibroblast strains that included those from the orbit or various anatomic regions of skin. Included were strains from the pretibial skin as well as the abdominal wall and the neck. The latter two sites rarely manifest Graves' disease. A substantial fraction of the GD-IgG-provoked T cell migration activity in most of these strains was resistant to neutralization with anti-IL-16.

To determine whether neutralizing antibodies directed at other chemoattractant molecules could block the residual activity, the effect of anti-RANTES on GD-IgG-provoked T cell migration activity was investigated (FIG. 15). GD-IgG up-regulated both IL-16 and RANTES proteins in eight Graves' disease-derived fibroblast strains while RANTES was undetectable in two of the Graves' disease strains exhibiting marked IL-16 inductions. GD-IgG failed to up-regulate T cell chemotaxis or to induce either IL-16 or RANTES protein in one Graves' disease strain (orbital strain 9) and in any of the 5 culture strains derived from donors without known thyroid disease. The control IgG failed to induce either IL-16 or RANTES expression in any of the fibroblast strains tested. In contrast, IL-1β induced T cell chemoattraction in all fibroblast strains, consistent with Sciaky et al., supra, 2000.

EXAMPLE II

Rheumatoid Arthritis and Graves' Disease are each Associated with Disease-Specific IcGs that Induce a Chemotactic Response and Chemokine Expression via the IGF-1R This example demonstrates that Rheumatoid Arthritis-IgGs (RA-IgGs)and GD-IgGs each induce a chemotactic response and chemokine expression in fibroblasts obtained from individuals afflicted with Rheumatoid Arthritis and Graves' Disease, respectively, and that this induction is mediated through IGF-1R.

Figure 7:
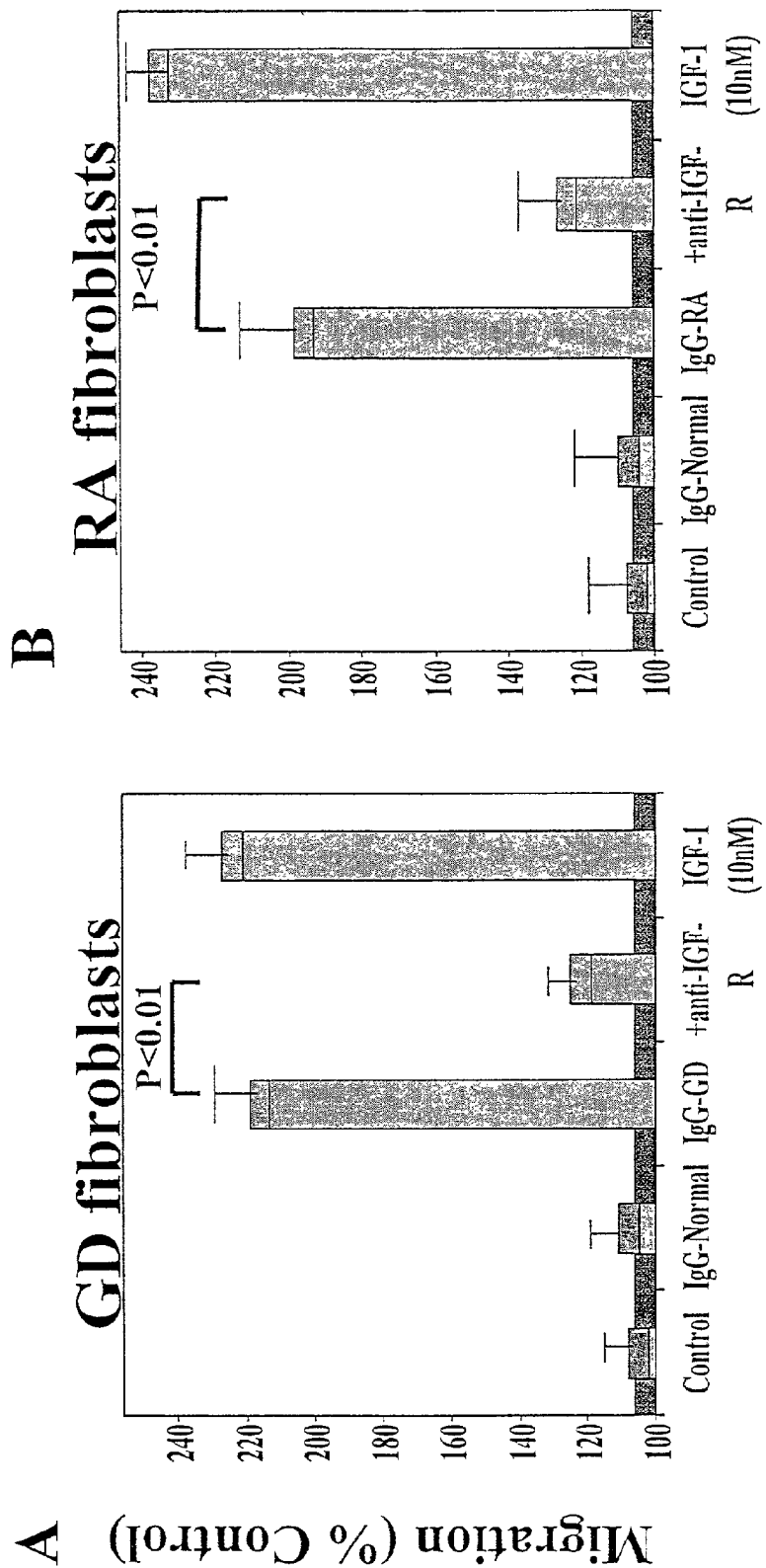
FIG. 7 shows that the induction of T cell chemotactic activity in fibroblasts obtained from (A) donors afflicted with Graves' disease is specific to GD-IgGs and is IGF-1R-dependent; (B) donors afflicted with Rheumatoid Arthritis is specific to RA-IgGs and is IGF-1R-dependent, and (C) donors afflicted with Osteoarthritis, an inflammatory connective tissue condition without an autoimmune component, is absent.
Figure 7:
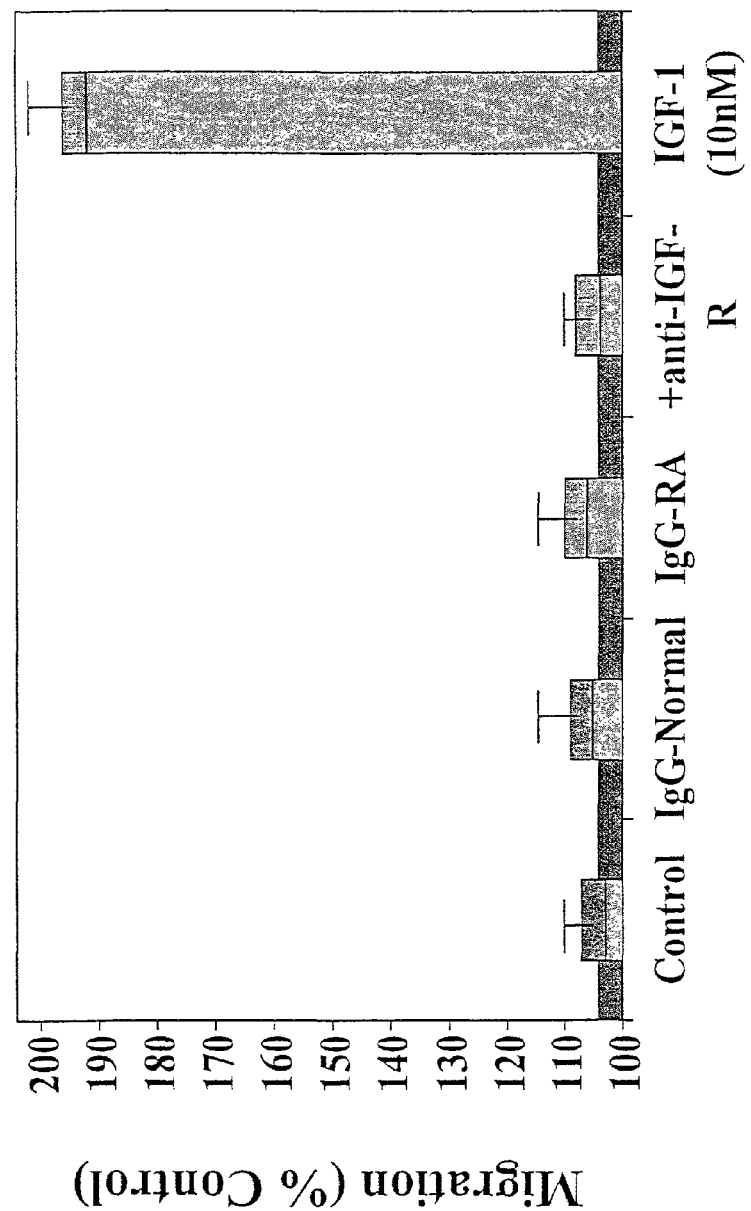

To determine whether T cell chemotaxis induced by RA-IgGs and GD-IgGs in fibroblasts obtained from individuals afflicted with Rheumatoid Arthritis and Graves' Disease, respectively, the presence of an anti-IGF-1R blocking antibody on T cell chemotaxis was observed utilizing the IGF-1R blocking antibody #36491 (Pharmingen, San Diego, Calif.). As shown in FIG. 7, the induction of chemotaxis by disease soecific IgGs can be mimicked by adding IGF-1 and further can be attenuated by adding IGF-1R.

Figure 8:
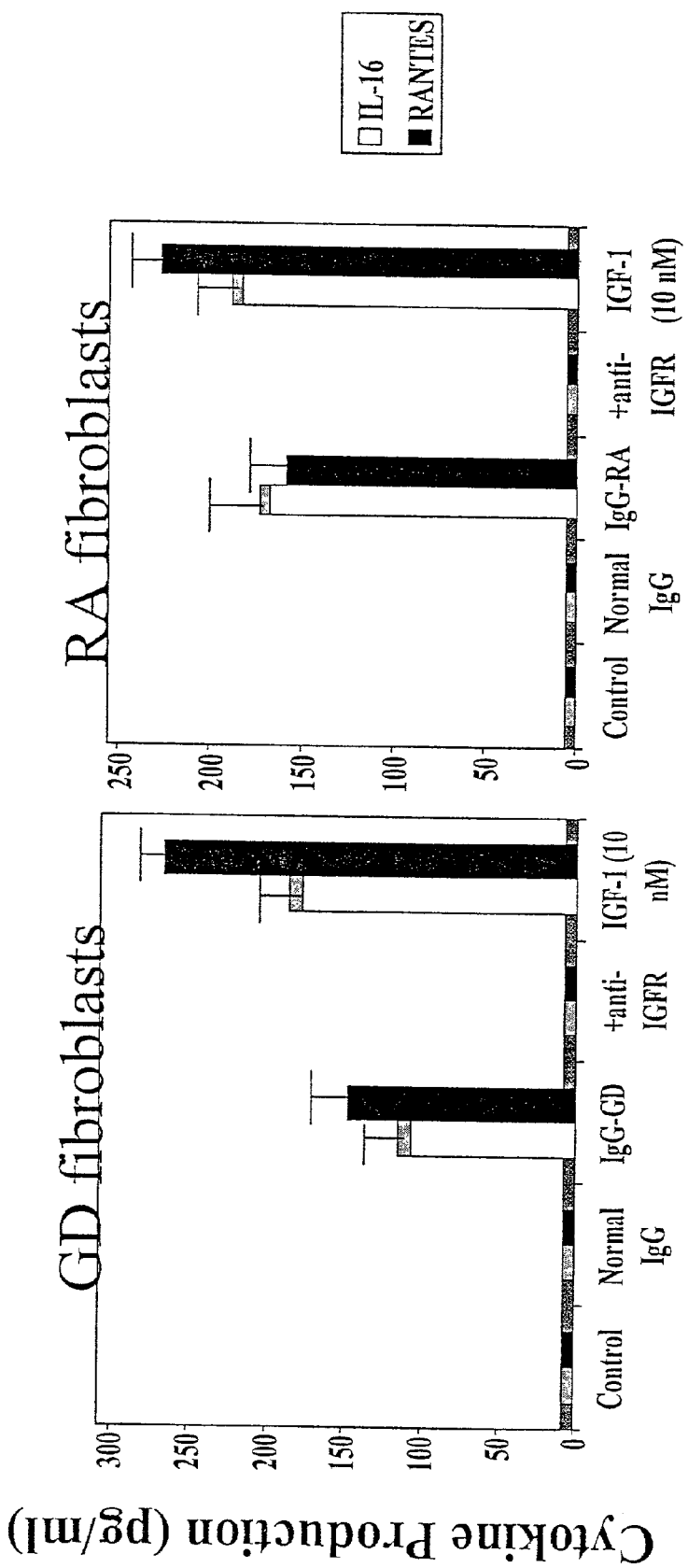
FIG. 8 shows IGF-1R-dependent induction of (A) IL-16 protein and RANTES protein by GD-IgGs in Graves' disease fibroblasts; and (B) IL-16 protein and RANTES protein by RA-IgGs in RA fibroblasts.
Figure 9:
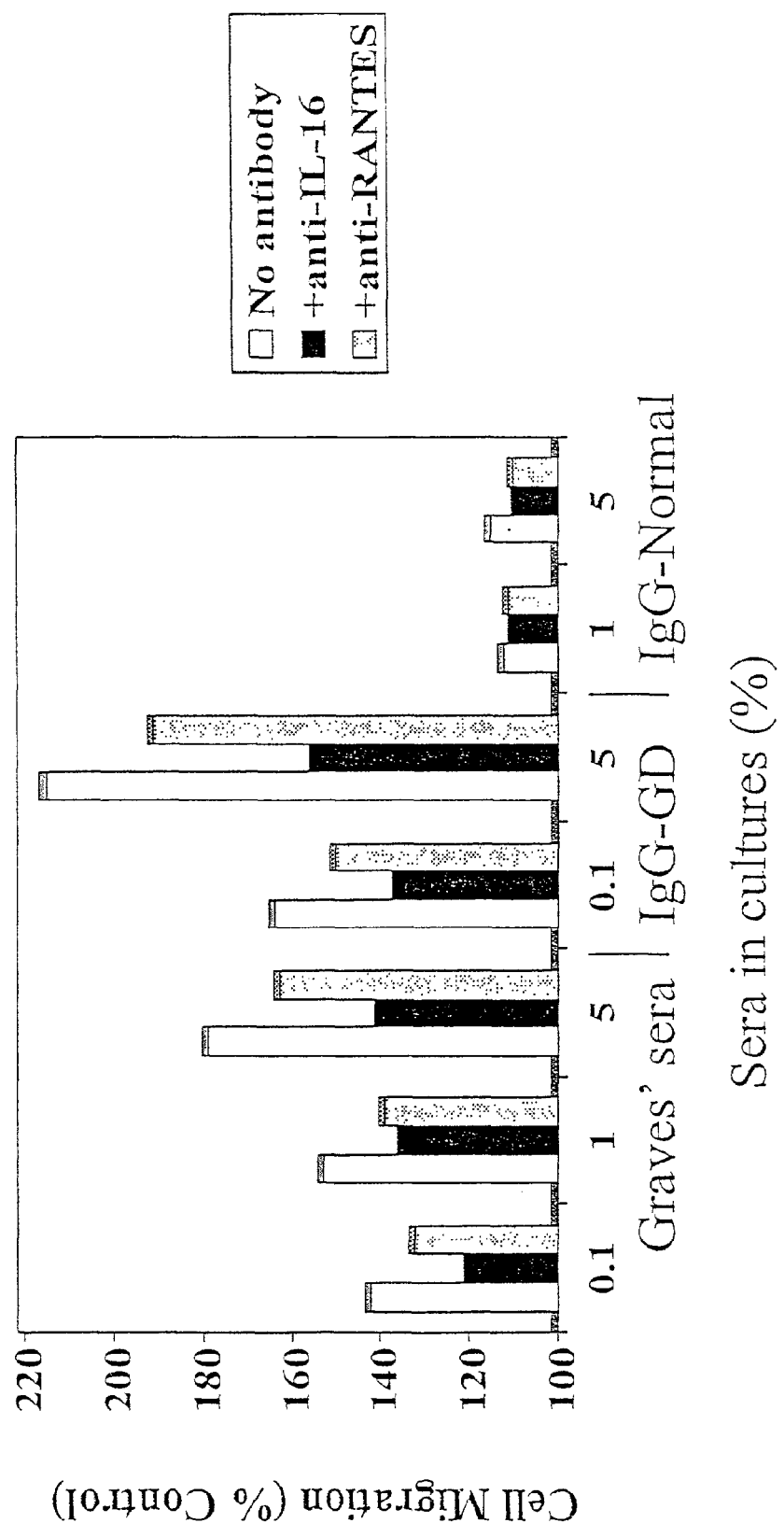
FIG. 9 shows that induction of T cell chemotactic activity in fibroblasts by serum is attributable to IgG, specific to donors with Graves' disease, and reduced in the presence of anti-IL-16-neutralizing antibody and anti-RANTES-neutralizing antibody.

To determine whether IGF-1R could be directly implicated in the mediation of GD-IgG-dependent and RA-IgG-dependent, respectively, increases in IL-16 and RANTES expression, cultures were challenged with the respective Igs in the absence or presence of the anti-IGF-1R blocking antibody, which binds the receptor subunit. As shown in FIG. 8, presence of the anti-IGF-1R blocking antibody results in the attenuation of the responses to disease-specific IgGs in both Graves' Disease and Rheumatoid Arthritis. Thus, the blockade of IGF-1R is associated with a near-complete attenuation of these two disease-specific-IgG provoked responses.

EXAMPLE III

Graves' Disease IgG Induces the Release of Newly Synthesized IL-16 in a Caspase-3 Dependent Manner This example demonstrates that GD-IgG can provoke release of newly synthesized IL-16 from Graves' disease fibroblasts in a caspase-3 dependent manner.

Figure 4:
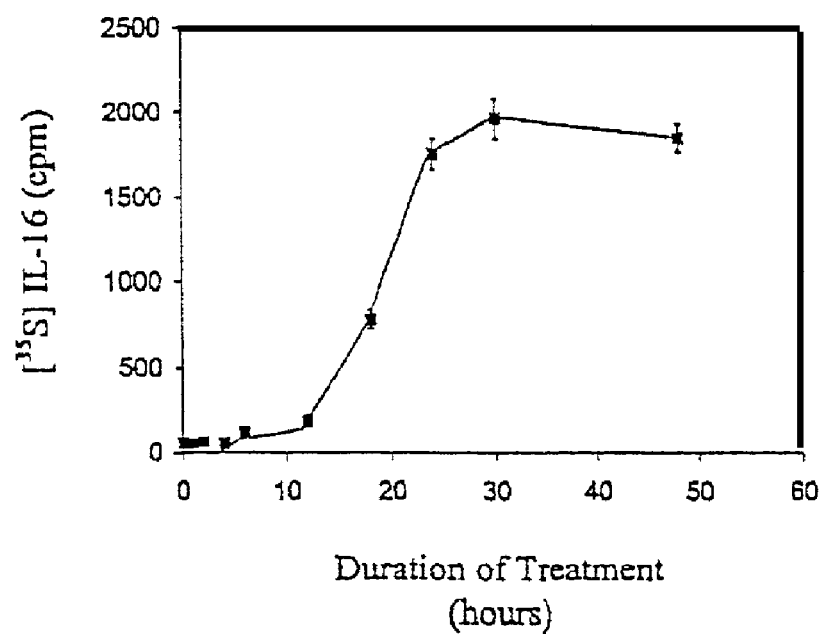
FIG. 4 shows that GD-IgG induces de novo synthesis of IL-16 in Graves' disease fibroblasts.

To determine whether GD-IgG induces the de novo synthesis of IL-16 in Graves' disease fibroblasts, confluent fibroblast monolayers, in this case from the skin, were treated with GD-IgG (100 ng/ml) for the durations indicated along the abscissa of FIG. 4. The confluent fibroblast monolayers were pulse-labeled with [35S]methionine (500 μCi/ml) for 6 h and immunoprecipitated with anti-IL-16 (clone 14.1, 5 μg/ml) conjugated to protein A beads, washed and counted for radioactivity. The data shown in FIG. 4 are expressed as the mean ±SD of three replicates. [$^{35}$S] IL-16 release was enhanced within 12 h of IgG addition to the culture medium. The maximal synthesis occured by 30 h when it was at least 100-fold above baseline and was sustained for the duration of the study (48 h). IL-16 protein is synthesized as a pro-molecule of 69 kDa that undergoes modification to the 56 kDa active molecule which is released from the cell (baier et al., *Proc. Natl. Acad. Sci. USA* 94:5273 (1997); Zhang et al., *J. Biol. Chem.* 273:1144 (1998)). In lymphocytes this processing involves a caspase-3 dependent cleavage (Zhang et al., supra, 1998). Moreover, in fibroblasts, the induction by IL-1β of IL-16 involves this enzyme (Sciaky et al., supra, 2000).

Figure 5:
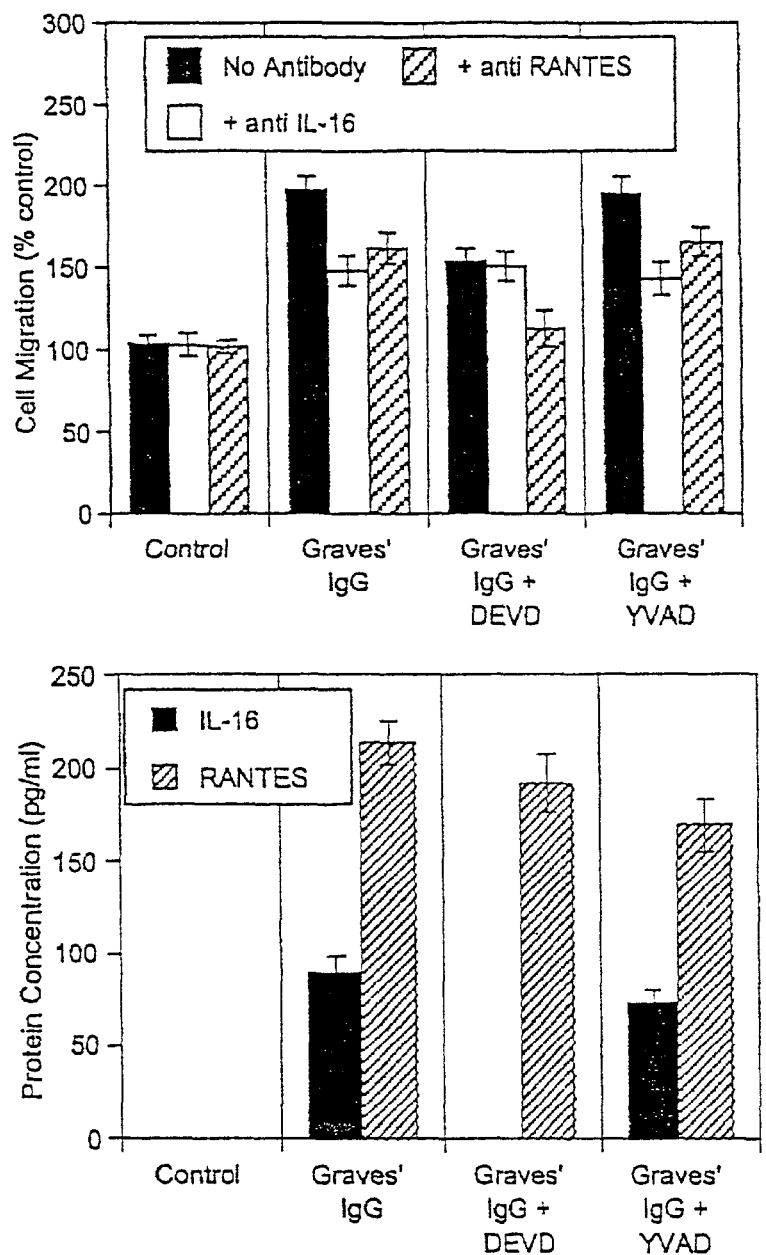
FIG. 5 shows that induction of (A) IL-16-dependent T cell migration and (B) IL-16 protein by GD-IgG in Graves' disease fibroblasts is dependent upon caspase-3 activity.

In order to determine whether inhibition of caspase-3 with a specific inhibitory peptide could block the GD-IgG release of IL-16 in Graves' disease fibroblasts, the peptide designated Ac-DEVD-CHO, a caspase-3-specific inhibitor was added to fibroblasts. In particular, confluent fibroblast monolayers were treated with GD-IgG (100 ng/ml) alone or in combination with the casapase-3 inhibitory peptide (Ac-DEVD-CHO, 100 μM) or a caspase-1 inhibitory peptide (Ac-YVAD-Ald, 100 μM). Media were collected and subjected to either the T cell migration assay (Top panel) or an IL-16 ELISA (bottom panel). Migration was determined in the absence or presence of anti-IL-16 (5 μg/ml) or anti-RANTES (5 μg/ml) antibodies. Data are expressed as the mean ±SD of triplicate determinations. As shown in FIG. 5, addition of the peptide designated Ac-DEVD-CHO to fibroblast medium resulted in a dramatic decrease in the lymphocyte migration ascribable to IL-16 and to the induction by IgG of IL-16 protein as determined in the ELISA assay. In contrast, the up-regulation of RANTES was unaffected. The caspase-1-specific peptide inhibitor, Ac-YVAD-Ald, failed to influence either IL-16 or RANTES activity or protein release into the medium.

EXAMPLE IV

GD-IGG Induction of IL-16 Expression and Release from Fibroblasts Involves a Rapamycin-Sensitive Pathway This example demonstrates that the induction of IL-16 protein by GD-IgG can blocked by rapamycin.

In order to determine whether GD-IgG induces chemoattractant expression in GD-fibroblasts by acting as a growth factor and binding an epitope on the surface of the fibroblast and initiating protein synthesis through the activation of one or more signaling pathways, the possibility of involvement of FRAP/mTOR pathway was investigated. The FRAP/mTOR pathway and the activation of the serine/threonine kinase p70$^{S6k}$ play central roles in mediating the effects provoked by multiple factors acting at the cell surface (Pullen and Thomas, *FEBS Letters* 410:78 (1997)). A prominent characteristic of this pathway is its susceptibility to inhibition by the macrolide, rapamycin (Brennan et al., *Mol. Cell. Biol.* 19:4729 (1999)). Significantly, rapamycin at a concentration of 20 nM, can block ca 50% of the chemoattractive activity elicited by GD-IgG, coinciding with an attenuation of IL-16-dependent T cell migration (FIG. 16). The induction of IL-16 protein by GD-IgG is blocked by rapamycin whereas that of RANTES is not.

To determine whether GD-IgG increased levels of activated p70$^{s6k}$, western blot immunoblot analysis with a primary antibody specific for p70$^{s6k}$ phosphorylated at Thr$^{389}$. Briefly, p70S6k activation was assessed by subjecting cellular protein from IgG activated fibroblasts to immunoblot analysis. Fibroblasts were allowed to proliferate to confluence in 60 mm plates. Following incubations with the test compounds indicated, monolayers were solubilized in a buffer containing 10 mM Tris-HCl (pH 7.5), 1 mM EDTA, 100 mM NaCl, 0.5% deoxycholate, 1% Triton X-100, 10% glycerol, 0.1% SDS, 2 mM Na3VO4, 20 mM NaP2O4, 1 mM NaF and 1 mM microcystin, 10 μg/ml aprotinin and 100 mM phenylmethylsulfonyl fluoride. Lysate samples normalized to their respective protein content were boiled in Laemmli buffer and subjected to sodium dodecyl sulfate-polyacrylamide gel electrophoresis according to the method described by Wang et al., *J. Biol. Chem.* 271:22718 (1996). The separated proteins were transferred to polyvinylidene difluoride membranes (bio-Rad) and subsequently incubated with primary phospho-specific anti-p70$^{S6k}$ Thr 389 (Cell Signaling Technology). Other aliquots of the sample were electrophoresed and blotted against a pan p70$^{s6k}$ antibody (Santa Cruz) or anti-actin antibody (Sigma). Following extensive washes at room temperature, the membranes were incubated with secondary, peroxidase-labeled antibodies for 1 hour. Following washes, the ECL (Amersham Corp.) chemiluminescence detection system was used to generate the relevant signals. The bands were analyzed densitometrically with a scanner.

Figure 6:
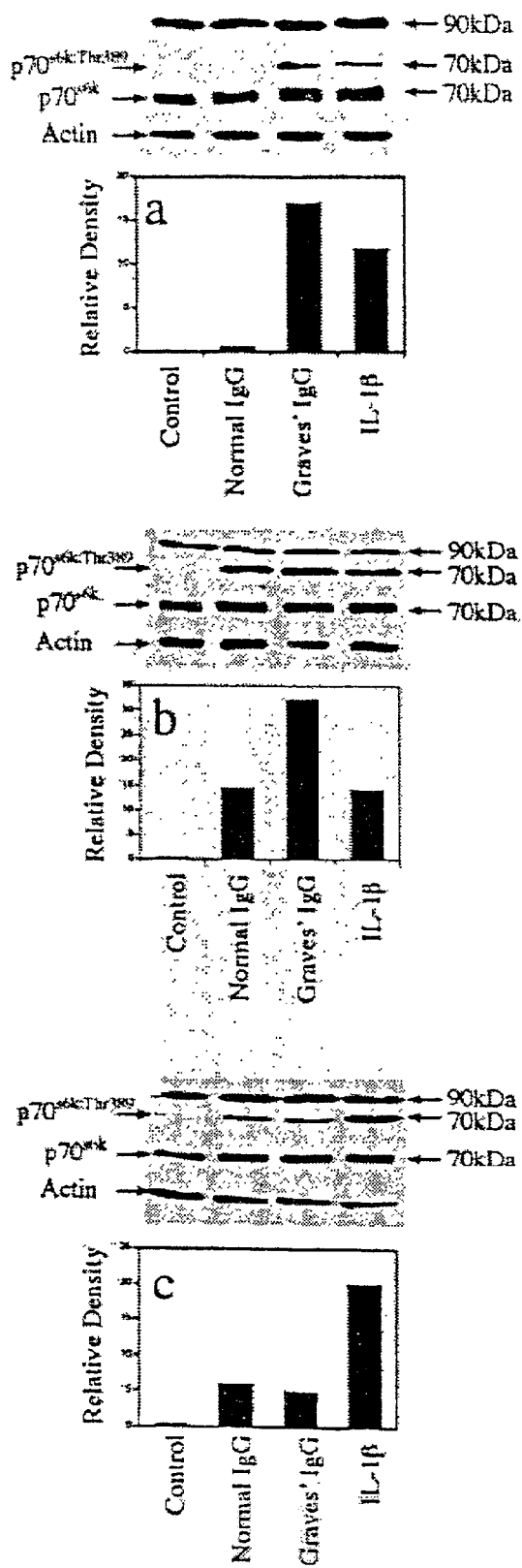
FIG. 6 shows that GD-IgG rapidly activates $p70^{s6k}$ $Thr^{389}$ phosphorylation in Graves' disease fibroblasts.

For the results shown in FIG. 6, confluent monolayers of orbital fibroblasts from two patients with Graves' disease (A and B) or a single donor with normal orbital tissue (C) were incubated with nothing (control), normal IgG (100 ng/ml), GD-IgG (100 ng/ml) or IL-1β (10 ng/ml) for 15 min, cells were rinsed and harvested in lysis buffer. Equivalent amounts of protein were subjected to western blot analysis, as described above, with pan anti-p70$^{s6k}$, phospho-specific anti-p70$^{s6k}$ Thr389, or anti-actin antibodies. Column heights represent p70$^{s6k}$ Thr389 signal densities corrected for their respective actin levels. As shown in FIG. 6, GD-IgG elicits an increase in activated p70$^{S6k}$. IgG from control subjects also increased phosphorylated p70$^{S6k}$, but the levels were considerably lower than those for GD-IgG. Moreover, normal fibroblasts challenged with either GD-IgG or control IgG failed to exhibit substantial p70$^{S6K}$ activation. Taken together, these findings demonstrate that p70$^{s6k}$ activation by IgG may alone be insufficient to up-regulate IL-16 expression. Given the ability of rapamycin to block, the activation of p70$^{s6k}$ is essential for the induction by GD-IgG of IL-16 in fibroblasts.

Glucocorticoids exert powerful modulatory actions on the expression of many pro-inflammatory molecules and they have an important therapeutic role in Graves' disease complicated with TAO. The impact of these steroids on the induction by GD-IgG of chemoattractant expression in fibroblasts was determined by adding glucocorticoid Dexamethasone (10 nM) to the medium in combination with GD-IgG and fibroblasts followed by a 16 h incubation. As shown in FIG. 16, the glucocorticoid could block both IL-16 and RANTES induction by GD-IgG.

EXAMPLE V

IcG Induction of IL-16 and RANTES in GD-Fibroblasts can be Attenuated by Blocking the IGF-1R This example demonstrates that the IGF-1R is directly involved in the activities exerted by GD-IgG in fibroblasts derived from Graves' disease patients.

Fibroblasts activated by pro-inflammatory cytokines express substantial T cell chemotaxis promoting activity (Skiaky et al., supra, 2000). Moreover, as described herein, GD-IgG isolated from individuals without or with overt TAO can activate fibroblasts from patients with Graves' disease to express high levels of IL-16 and RANTES.

Serum from patients with Graves' disease contains anti-TSHR antibodies. In order to determine whether TSHR represents the self-antigen relevant to these effects in fibroblasts, Graves' disease fibroblasts were treated with TSH (2 mU/ml) for 24 h and were then assayed for chemoattractant expression.

Figure 10:
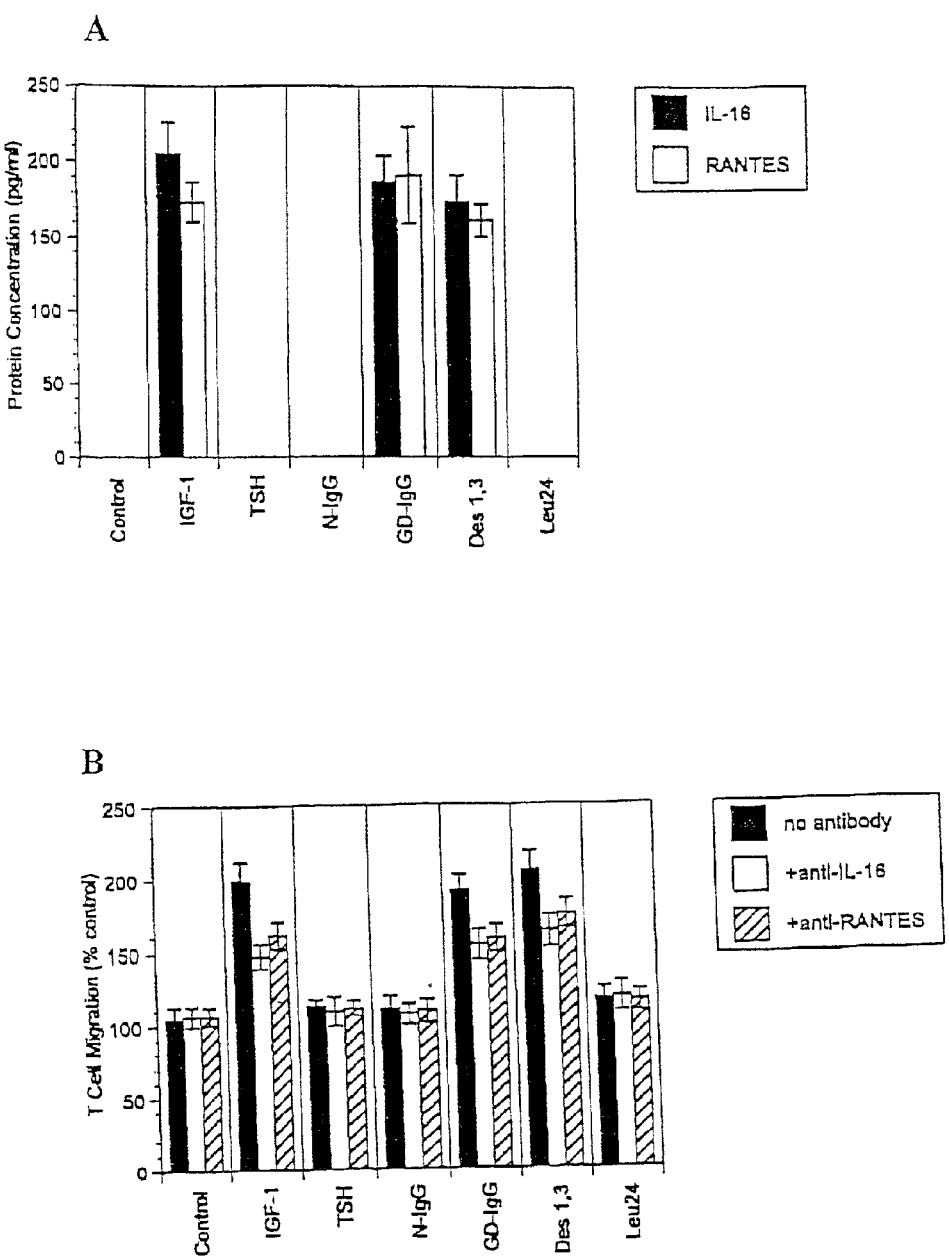
FIG. 10 shows induction of (A) IL-16 protein and RANTES protein by GD-IgGs, the IGF-1 analog des(1-3), and lack of induction by the IGF-1 analog [Leu24] IGF-1; and (B) T cell chemotactic activity in Graves' disease fibroblasts is attributable to GD-IgGs and signaled through the IGF-1R per se rather than through accessory binding proteins (IG-FBP).

As shown in FIG. 10, TSH failed to influence either IL-16 or RANTES expression. This result demonstrates that TSHR activation is not mediating the actions of GD-IgG on fibroblasts. IL-1 induces both IL-16 and RANTES levels and T cell chemotaxis in all fibroblast strains tested regardless of whether they were derived from patients with Graves' disease or from control subjects without known thyroid disease.

A large number of other compounds known to bind and activate receptors expressed by human fibroblasts were examined for their ability to induce IL-16 and RANTES, since their respective receptors would then represent candidate antigens for GD-IgG. Among those tested, IGF-1 (10 nM) dramatically increased IL-16 and RANTES-dependent T cell migration and the levels of both chemoattractants after a 24 h treatment of fibroblast cultures (FIG. 10). The magnitude of the inductions was similar to that observed with IL-1 (FIG. 10).

To define the specificity of the IGF-1 effect, the IGF-1R-specific ligands Des (1-3) IGF-1 and Leu24 IGF-1 were also tested and found to induce chemoattractant expression. FIG. 10 shows induction of IL-16 protein and RANTES protein by GD-IgGs and the IGF analog des(1-3), a truncated form of IGF-1 that lacks the N-terminal tripeptide and is a IGF-1R-specific ligand with much reduced affinity for IGF binding proteins (IGFBP) compared to natural IGF-1 as described by Bang et al., *Acta Endocrinologica* 124:620-629 (1991), which is incorporated herein by reference. [Leu24] IGF-1 is an analog of human IGF-1 with the substitution of a Leu for a Tyr at position 24. [Leu24] IGF-1 has a strongly reduced affinity for the IGF-1R and a reduced affinity for some IGFBP. As shown in panel B of FIG. 10, T cell chemotactic activity in Graves' disease fibroblasts is attributable to GD-IgGs and signaled through the IGF-1R per se rather than through accessory binding proteins (IGFBP).

Figure 11:
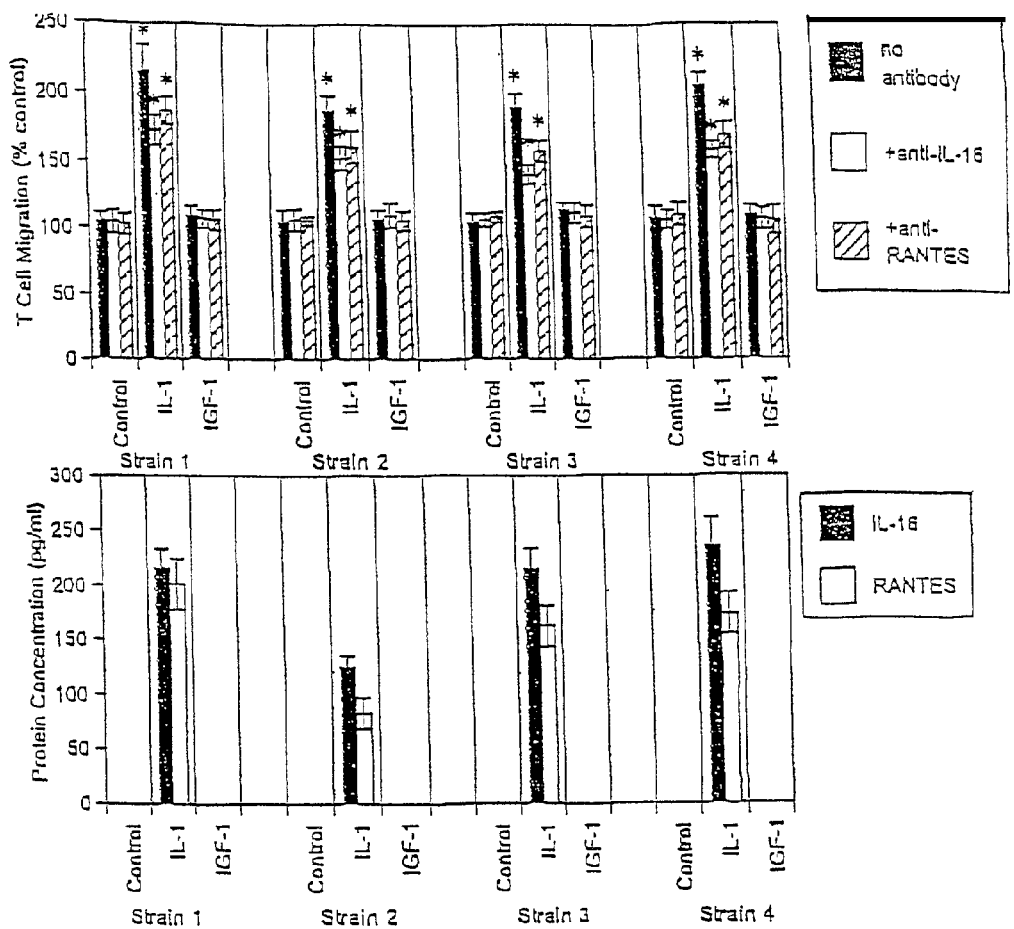
FIG. 11 shows four normal fibroblast strains treated with either IGF-1 or IL-1β for 24 hours and subsequently assayed for (A) T cell migration promoting activity; and (B) for IL-16 and RANTES content in the respective ELISAs.

To test whether IGF-1 activities are similarly restricted, several different fibroblast strains obtained from normal donors were tested. As shown in FIG. 11, none of these fibroblasts responded to IGF-1 treatment under identical conditions to those used in studies with Graves' disease fibroblasts. Thus, intrinsic differences in Graves' disease and normal fibroblasts underlie the responses to GD-IgG and exogenous IGF-1, showing that IGF-1 and GD-IgG act through the same or a related pathway. IL-1 induces both IL-16 and RANTES levels and T cell chemotaxis in all fibroblast strains tested regardless of whether they were derived from patients with GD or from control subjects without known thyroid disease.

A large number of other compounds known to bind and activate receptors expressed by human fibroblasts were examined for their ability to induce IL-16 and RANTES, since their respective receptors would then represent candidate antigens for GD-IgG. Among those tested, IGF-1 (10 nM) dramatically increased IL-16 and RANTES-dependent T cell migration and the levels of both chemoattractants after a 24 h treatment of fibroblast cultures. The magnitude of the inductions was similar to that observed with IL-1.

Figure 12:
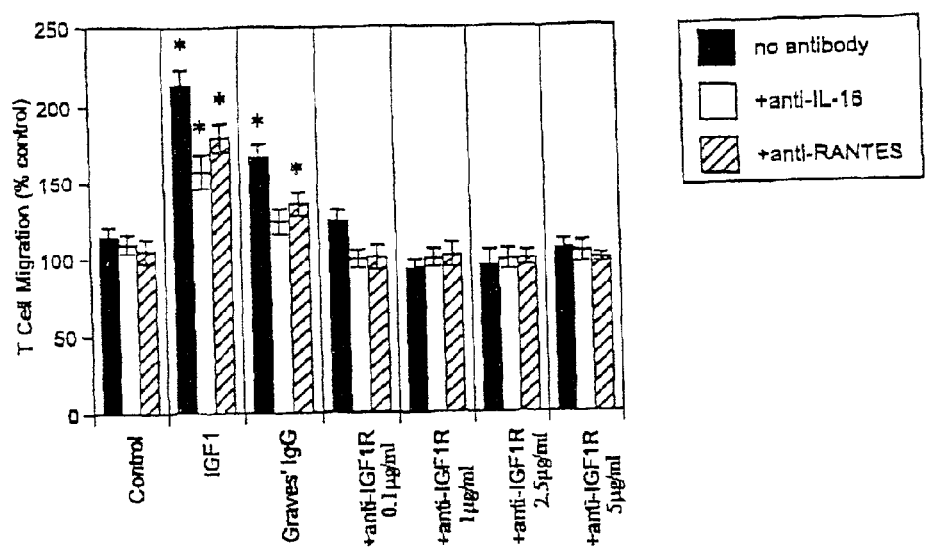
FIG. 12 shows that blockade of IGF-1R is associated with a near-complete attenuation of the GD-IgG provoked responses.

To determine whether IGF-1R participates directly in the mediation of GD-IgG dependent increases in IL-16 and RANTES expression, cultures were challenged with Igs in the absence or presence of a highly specific receptor blocking antibody, clone 1H7, which binds the receptor subunit. As shown in FIG. 12, low concentrations of the antibody block the action of GD-Ig. The concentrations of 1H7 tested ranged from 0.1 μg/ml to 5 μg/ml. Even at the lowest concentration used, the attenuation of the responses to GD-IgGs was 90%. Thus, the blockade of IGF-1R is associated with a near-complete attenuation of the GD-IgG provoked responses.

Figure 14:
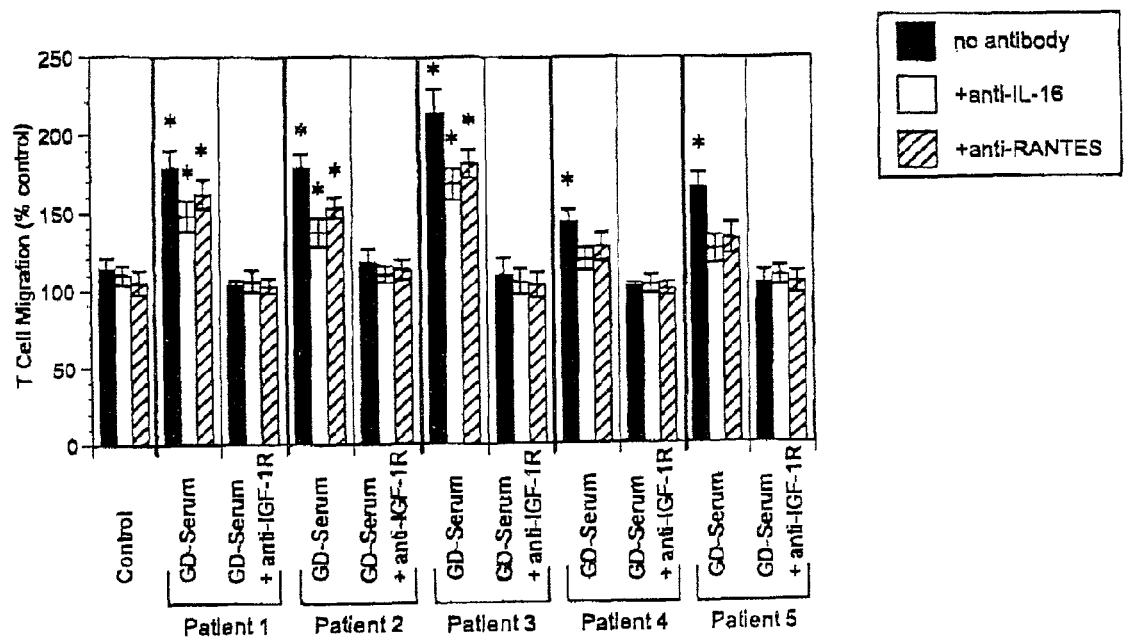
FIG. 14 shows the induction of IL-16-dependent and RANTES-dependent T cell chemotaxis in five sera samples obtained from a single strain of Graves' disease fibroblasts and the effect of adding anti-IGF-1R antibodies, which blocked these inductions.

To determine whether the impact of Graves' disease serum on IGF-1R-mediated chemoattractant expression could be generalized to the sera of most patients with the disease, several samples were tested on a single strain of Graves' disease fibroblasts. As FIG. 14 demonstrates, all five sera samples provoked inductions of IL-16- and RANTES- dependent T cell chemotaxis and in all cases, anti-IGF-1R antibodies blocked these inductions. Moreover, the IgGs up-regulated the levels of the two proteins, as assessed by the cytokine-specific ELISAs.

Another, more direct approach to demonstrating the role of IGF-1R in mediating the GD-IgG effects on chemotaxis produced by fibroblasts would involve targeting the receptor with a dominant-negative (DN) mutant and interrupting its expression. Cultures were transiently transfected with the mutant IGF-1R, 486/STOP or the empty vector as a control and determining the impact the DN has on cellular responses to GD-IgG. Briefly, cultures were allowed to proliferate to 80% confluence in medium containing 10% FBS. The plasmid containing 486/STOP DN IGF-1R was transiently transfected into the cells using LipofectAMINE PLUS system (Invitrogen, San Diego, Calif.). In particular, 0.75 μg of the plasmid and 0.1 μg of PRL-TK vector DNA (Promega), serving as a transfection efficiency control, were mixed with PLUS reagent for 15 minutes before being combined with LipofectAMINE PLUS for another 15 minutes. Some cultures received empty vector DNA as a control. The DNA-lipid mixture was added to the culture medium for 3 h at 37° C. Dulbeccols modified Eagle's medium containing 10% FBS replaced the transfection mixture overnight. Transfected cultures were then serum-starved and some received GD-IgG or normal IgG for 16 h. Media samples were collected and frozen until they were assayed for T cell migration promoting activity or for IL-16 and RANTES content in the respective ELISAs.

Figure 13:
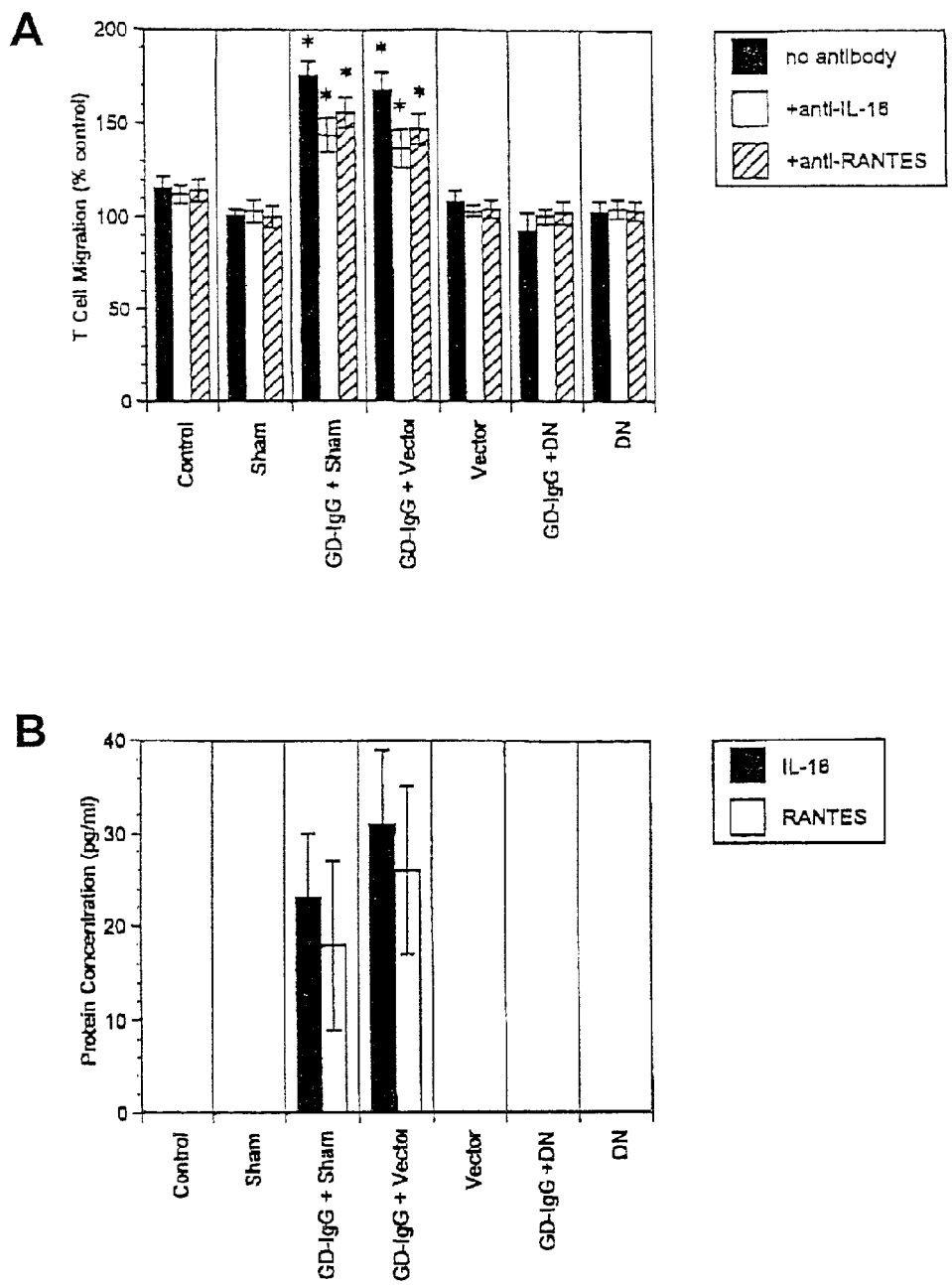
FIG. 13 shows that the dominant negative mutant of IGF-1R designated IGF-1R,486/STOP blocks (A) the induction by GD-IgG of T cell chemotactic activity; and (B) the induction of IL-16 protein and RANTES protein content.

As shown in FIG. 13, IFF-1R DN inhibited induction by GD-IgG of T cell chemotactic activity and attenuated the induction of both IL-16 and RANTES by GD-IgG. In contrast, sham-transfections and those with empty vector failed to alter the effects of GD-IgG. Taken together with the results with the IGF-1R blocking antibodies and the IGF-1R-specific agonists described above, this result confirms that the IGF-1R receptor appears to be directly involved in the activities exerted by GD-IgG in fibroblasts derived from Graves' disease patients.

EXAMPLE VI

Induction of IL-16 in GD Fibroblasts does not Involve Increases in IL-16 mRNA

This example shows that induction of IL-16 in Graves' disease fibroblasts does not involve increases in IL-16 mRNA and, that induction of RANTES in these cells is mediated at the pre-translational level.

GD-IgG induction of IL-16 and RANTES in fibroblasts involves divergent signaling pathways. As described herein, the former up-regulation is susceptible to rapamycin, an inhibitor of the FRAP/mTOR/$p70^{s6k}$ pathway, whereas the latter is unaffected by the drug. Fibroblasts are known to express high levels of IL-16 mRNA constitutively and the levels are not affected by treatment with pro-inflammatory cytokines that up-regulate IL-16 protein synthesis and T cell chemotaxis attributed to it. As shown in the northern blot in FIG. 14, GD-IgG fails to increase the high levels of IL-16 mRNA over the course of the experiment (up to 16 h). IL-1β also failed to influence steady-state transcript levels. In contrast, RANTES mRNA is not detected under basal culture conditions but there occurs a substantial and time-dependent induction of the transcript with IgG treatment. There also occurred a strong induction in cultures treated with IL-1β.

For the Northern analysis, fibroblasts were cultivated in 100-mm diameter plates to a confluent state and were then treated with the test agents. Briefly, cellular RNA was extracted from rinsed monolayers by the method of Chomczynski and Sacchi, *Anal Biochem.* 162:156-159 (1987), with an RNA isolating system purchased from Biotecx (Houston, Tex.). The nucleic acid was subjected to electrophoresis through denaturing 1% agarose, formaldehyde gels. Integrity of the RNA was established by determining the 260/280 spectroscopic ratios and by staining the electrophoresed samples with ethidium bromide and inspecting them under UV light. The RNA was transferred to Zeta-probe membrane (bio-Rad), and immobilized samples were hybridized with [$^{32}$p] dCTP-labeled PGHS-1, PGHS-2, p23 and mPGES cDNA probes generated by the random primer method. Hybridization was conducted in a solution containing 5X SSC, 50% formamide, 5X Denhardt's solution, 50 mM phosphate buffer (pH 6.5), 1% SDS, and 0.25 mg/ml salmon sperm at 48° C. overnight. Membranes were washed under high stringency conditions, and then the RNA/DNA hybrids were visualized by autoradiography on X-Omat film (Kodak, Rochester, N.Y.) following exposure at −70° C. Bands resulting from radioactive hybrids were scanned by densitometry. Membranes were then stripped according to the instructions of the manufacturer and rehybridized with a GAPDH cDNA probe, and the band densities were normalized to this signal.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of reducing the severity of Graves' disease (GD) comprising administering an effective amount of a blocking antibody specific for Insulin Like Growth Factor-1 Receptor (IGF-1R) to an individual, wherein said blocking antibody binds to a receptor subunit of the IGF-1R, and wherein said blocking antibody inhibits activation of fibroblasts caused by interaction between IGF-1R and an endogenous immunoglobulin.

2. The method of claim 1, wherein said endogenous immunoglobulin is IgG.

3. The method of claim 1, wherein said reduction in severity comprises reducing the severity of a manifestation of Graves' disease (GD).

4. The method of claim 3, wherein said manifestation of Graves' disease (GD) is associated with connective tissue remodeling.

5. The method of claim 4, wherein said manifestation of Graves' disease (GD) is selected from the group consisting of Thyroid-associated ophthalmology (TAO) and dermopathy.

6. The method of claim 1, wherein said antibody is selected from the group consisting of humanized antibody, single chain antibody, chimeric antibody, bifunctional antibody and complementarity determining region-grafted (CDR-grafted) antibody.

* * * * *